(12) United States Patent
Taguchi

(10) Patent No.: US 9,377,853 B2
(45) Date of Patent: Jun. 28, 2016

(54) INFORMATION PROCESSING APPARATUS AND INFORMATION PROCESSING METHOD

(71) Applicant: FUJITSU LIMITED, Kawasaki-shi, Kanagawa (JP)

(72) Inventor: Akinori Taguchi, Kawasaki (JP)

(73) Assignee: FUJITSU LIMITED, Kawasaki (JP)

( * ) Notice: Subject to any disclaimer, the term of this patent is extended or adjusted under 35 U.S.C. 154(b) by 6 days.

(21) Appl. No.: 14/469,693

(22) Filed: Aug. 27, 2014

(65) Prior Publication Data

US 2015/0070268 A1    Mar. 12, 2015

(30) Foreign Application Priority Data

Sep. 11, 2013    (JP) .................................. 2013-187905

(51) Int. Cl.
| | |
|---|---|
| *G06F 3/01* | (2006.01) |
| *A61B 3/113* | (2006.01) |
| *G02B 27/00* | (2006.01) |
| *G06F 3/0483* | (2013.01) |
| *G06F 3/0484* | (2013.01) |
| *G06F 3/0481* | (2013.01) |
| *G06F 3/0485* | (2013.01) |

(52) U.S. Cl.
CPC ................ *G06F 3/013* (2013.01); *A61B 3/113* (2013.01); *G02B 27/0093* (2013.01); *G06F 3/0481* (2013.01); *G06F 3/0483* (2013.01); *G06F 3/0485* (2013.01); *G06F 3/04842* (2013.01)

(58) Field of Classification Search
CPC ........ G06F 3/013; G06F 3/0483; A61B 3/113
See application file for complete search history.

(56) References Cited

U.S. PATENT DOCUMENTS

| | | | | |
|---|---|---|---|---|
| 6,204,828 | B1* | 3/2001 | Amir ....................... | G06F 3/013 345/156 |
| 2010/0191727 | A1* | 7/2010 | Malik ............... | G06F 17/30867 707/734 |
| 2010/0205567 | A1* | 8/2010 | Haire ....................... | G06F 8/38 715/840 |
| 2012/0173999 | A1 | 7/2012 | Invernizzi | |

(Continued)

FOREIGN PATENT DOCUMENTS

| | | |
|---|---|---|
| EP | 0816980 | 1/1998 |
| EP | 1679577 | 7/2006 |

(Continued)

OTHER PUBLICATIONS

Extended European Search Report dated Jan. 29, 2015 in European Patent Application No. 14182913.5.

*Primary Examiner* — Quan-Zhen Wang
*Assistant Examiner* — Dong Hui Liang
(74) *Attorney, Agent, or Firm* — Staas & Halsey LLP

(57) ABSTRACT

An information processing apparatus includes: a memory, and a processor coupled to the memory and configured to: identify an end position of a last line of a plurality of lines in an object for reading displayed on a display screen, the object being subjected to determination of whether the object has been finished reading by a user based on detecting movement of a gaze position of the user on a display screen, determine a display position at which movement of the gaze position that is greater than or equal to a given distance from the identified end position is detected, and display a display object at the determined display position on the display screen, the display object being destination of the gaze point after the object has been finished reading.

15 Claims, 27 Drawing Sheets

(56) References Cited

U.S. PATENT DOCUMENTS

| | | | | |
|---|---|---|---|---|
| 2012/0256967 A1* | 10/2012 | Baldwin | | G06F 3/013 345/684 |
| 2013/0176208 A1 | 7/2013 | Tanaka et al. | | |
| 2014/0125585 A1* | 5/2014 | Song | | G06F 3/013 345/156 |
| 2015/0077334 A1* | 3/2015 | Mihara | | G06F 17/211 345/156 |
| 2016/0094705 A1* | 3/2016 | Vendrow | | H04M 1/72547 382/103 |

FOREIGN PATENT DOCUMENTS

| | | |
|---|---|---|
| EP | 2600220 | 6/2013 |
| JP | 08-22385 | 1/1996 |
| JP | 2006-107048 | 4/2006 |

\* cited by examiner

FIG. 16

| TIME | FIRST DETERMINATION AREA | | SECOND DETERMINATION AREA | | THRESHOLD | NUMBER OF LINES | DETERMINATION FLAG |
|---|---|---|---|---|---|---|---|
| | COORDINATES A | COORDINATES B | COORDINATES A | COORDINATES B | | | |
| 07/26/2013/13:00 | (xa, ya) | (xb, yb) | (xc, yc) | (xd, yd) | Mth | 9 | ON |
| ... | ... | ... | ... | ... | M2th | 1 | OFF |
| | | | | | ... | ... | ... |

FIG. 27
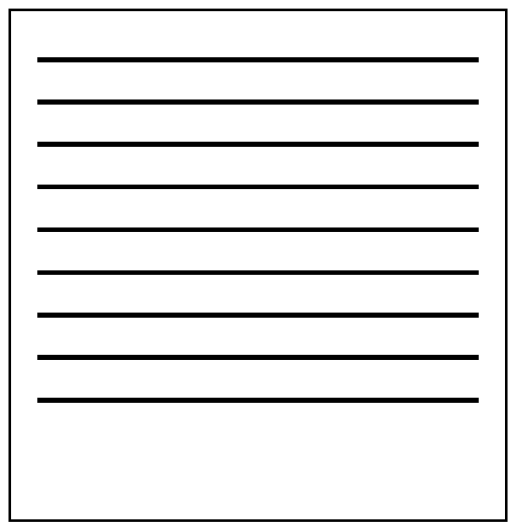
FIRST DOCUMENT
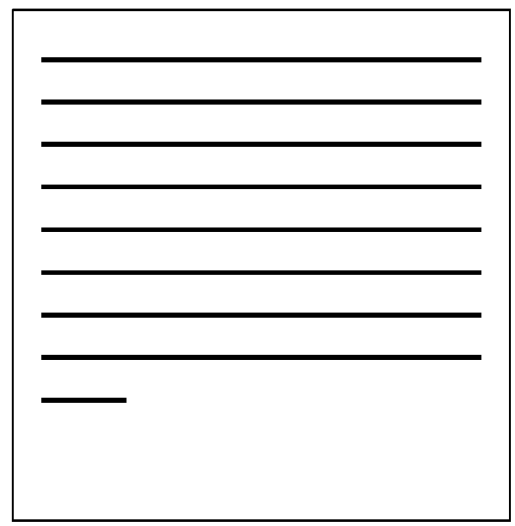
SECOND DOCUMENT

INFORMATION PROCESSING APPARATUS AND INFORMATION PROCESSING METHOD

CROSS-REFERENCE TO RELATED APPLICATION

This application is based upon and claims the benefit of priority of the prior Japanese Patent Application No. 2013-187905 filed on Sep. 11, 2013, the entire contents of which are incorporated herein by reference.

FIELD

The embodiments discussed herein are related to technology for determining whether an object for reading has been read.

BACKGROUND

As a screen rendering and updating method for information terminals such as personal computers, tablets, and kiosk terminals, technology that detects the gaze of a user and switches display content on the screen or performs a scroll operation in accordance with the gaze movement is available. Specifically, display on the screen is switched or the screen is scrolled after determining whether a specific area or the like has been read, thereby moderating the operation burden on the user.

In addition, the following technology that performs gaze-based screen control or the like is available. That is, a determination area is provided on an object for reading, such as text, content or the like. In the case where the coordinates of the gaze of a user are detected in that determination area, it is determined that the user is referring to that determination area. In the case where the order of parts to which the user has referred matches a predetermined order, it is determined that the user has read the object for reading, and gaze-based screen control or the like is performed.

SUMMARY

According to an aspect of the invention, an information processing apparatus includes: a memory, and a processor coupled to the memory and configured to: identify an end position of a last line of a plurality of lines in an object for reading displayed on a display screen, the object being subjected to determination of whether the object has been finished reading by a user based on detecting movement of a gaze position of the user on a display screen, determine a display position at which movement of the gaze position that is greater than or equal to a given distance from the identified end position is detected, and display a display object at the determined display position on the display screen, the display object being destination of the gaze point after the object has been finished reading.

The object and advantages of the invention will be realized and attained by means of the elements and combinations particularly pointed out in the claims.

It is to be understood that both the foregoing general description and the following detailed description are exemplary and explanatory and are not restrictive of the invention, as claimed.

BRIEF DESCRIPTION OF DRAWINGS

FIG. 16 is a diagram illustrating an example of data stored in a third data storage unit;

FIG. 27 is a diagram illustrating exemplary documents processed in a fourth embodiment;

DESCRIPTION OF EMBODIMENTS

Hereinafter, embodiments will be described with reference to the drawings.

While inventing the present embodiments, observations were made regarding a related art. Such observations include the following, for example.

In the case of such technology, when no coordinates of the gaze are detected in a determination area on text or content, as an example of an object for reading, subjected to determination of whether the text or content has been read, whether the user has read the text or content is undeterminable. For example, if the accuracy of the coordinates of the gaze position, output by a gaze detecting device, is relatively high, it is possible to determine in a determination area that, after the user has read the first line, the user has read the second line. However, the accuracy of the coordinates of the gaze position, output by the gaze detecting device, may be low, and a detection error may be rougher than the size of characters of the text (each line) or content. In such a case, the gaze position may not be accommodated in the determination area or may move across lines. Even if the user has finished reading the text or content, if the coordinates of the gaze position output by the gaze detecting device are simply tracked, it is impossible to detect whether the user has finished reading the text or content.

Accordingly, it is an object in one aspect of embodiments discussed herein to provide techniques for performing display to determine whether an object for reading, such as text, content or the like, has been finished reading, even when the accuracy of the coordinates of a gaze position, output by a gaze detecting device, are relatively low.

First Embodiment

Figure 1:
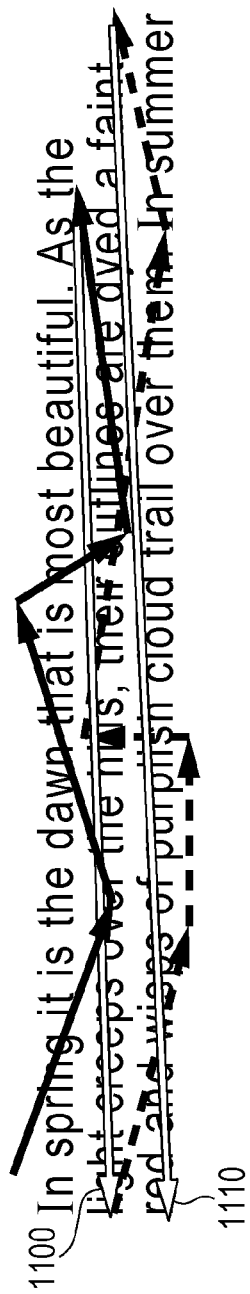
FIG. 1 is a diagram for describing gaze movement in embodiments.

In a first embodiment, even when the accuracy of the coordinates of a gaze position, output by a gaze detecting device, are relatively low, in the case of text written from left to right, as an example of text of a line configuration, such as that illustrated in FIG. 1, when a user reads the next line, the gaze moves from right to left, such as that indicated by arrows 1100 and 1110. This embodiment pays attention to the occurrence of such a gaze movement. By counting the number of occurrences of movement of the gaze position, which occurs when a user reads text and which corresponds to a newline (may also be referred to as a "line break"), whether text in a determination area has been read (has been finished reading) is determined.

However, as is clear from the example illustrated in FIG. 1, the arrows 1100 and 1110 occur in text including three lines, but no newline is detected after the last line (third line) has been read since there is no line next to the last line. Thus, if no special measures are taken, it is difficult to check whether the user has read the text to the last line.

Figure 2:
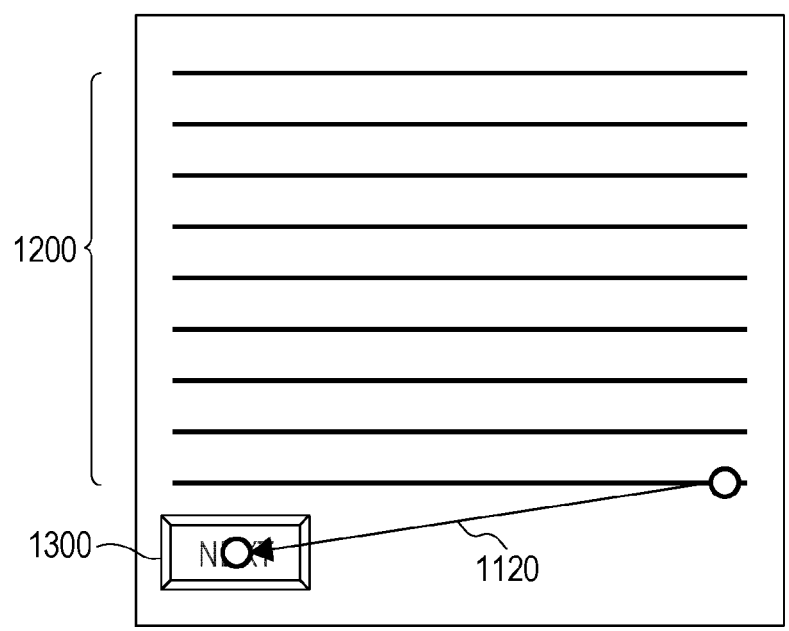
FIG. 2 is a diagram for describing a layout in the embodiments.

To this end, as schematically illustrated in FIG. 2, a button 1300 for entering that text 1200 including a plurality of lines has been read is displayed at an appropriate position. Specifically, the button 1300 is displayed near the beginning (the left end in this case) of the bottom line of the text 1200 written from left to right. Accordingly, in this embodiment, upon completion of reading the last line, the gaze moves from the end (the right end in this case) of the last line to the button 1300, and this movement 1120 is detectable in the same manner as a newline, thereby making it possible to determine that the user has read the text 1200 to the last line.

In this embodiment, after the button 1300 is arranged to enable such a determination, accordingly, a process for determining whether text has been read is executed.

Figure 3:
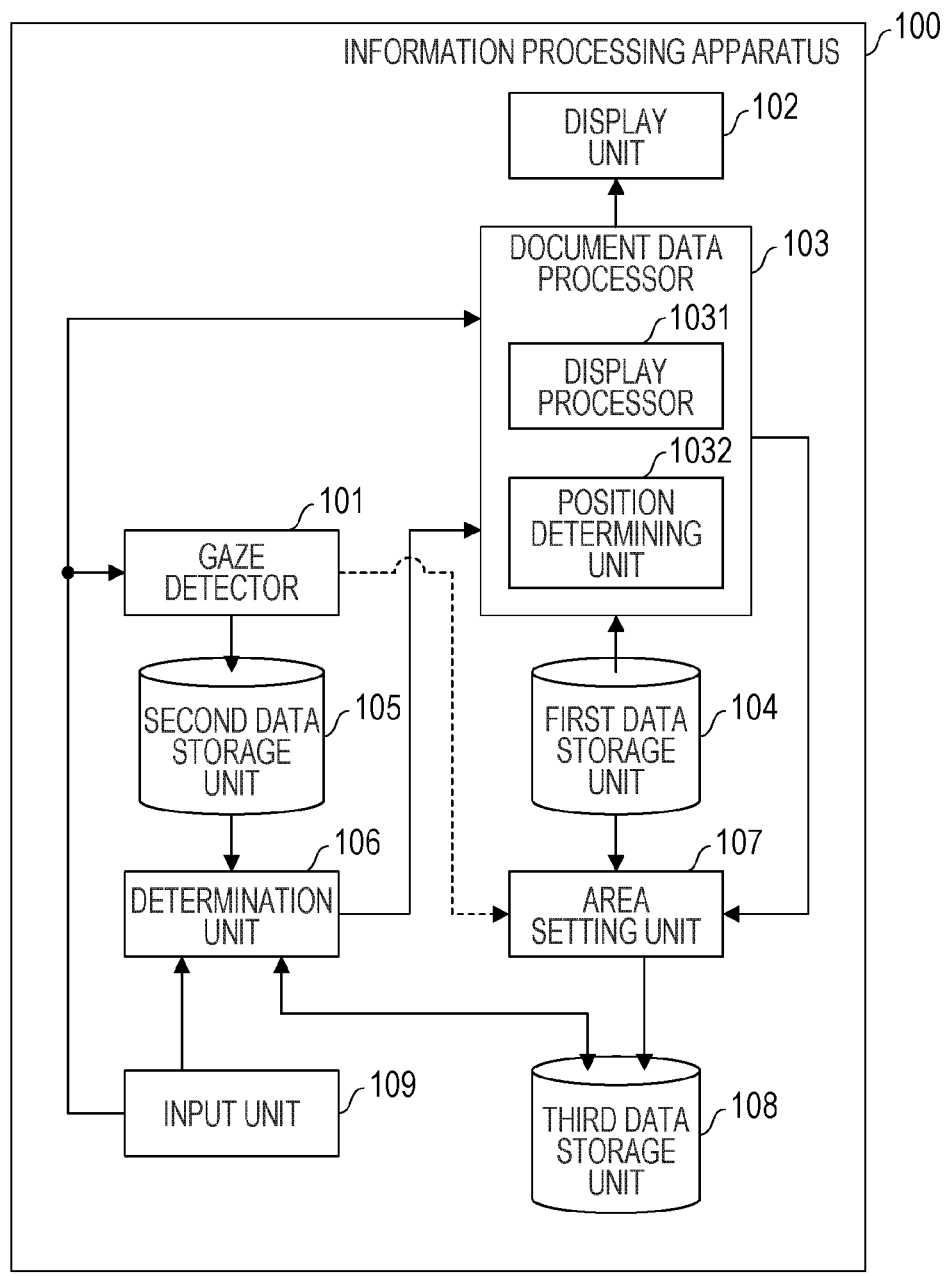
FIG. 3 is a functional block diagram of an information processing apparatus according to the embodiments.

FIG. 3 is a functional block diagram of an information processing apparatus according to this embodiment. An information processing apparatus 100 according to this embodiment includes a gaze detector 101, a display unit 102, a document data processor 103, a first data storage unit 104, a second data storage unit 105, a determination unit 106, an area setting unit 107, a third data storage unit 108, and an input unit 109.

The document data processor 103 includes a display processor 1031 and a position determining unit 1032.

The gaze detector 101 detects the coordinates of the gaze position on a display screen of the display unit 102, and stores the coordinates in the second data storage unit 105. In this embodiment, since the gaze detector 101 may be configured with any available mechanism and algorithm, a detailed description thereof is omitted.

The first data storage unit 104 stores text data subjected to determination of whether a user has read the text, range data set for the text, and setting data. The display processor 1031 of the document data processor 103 reads the text data stored in the first data storage unit 104, and outputs the data to the display unit 102. At this time, the position determining unit 1032 of the document data processor 103 uses the setting data stored in the first data storage unit 104 to execute a process of determining the arrangement position of the above-mentioned button 1300 and a process of determining a determination threshold for the last line, which is used in a process of determining whether text has been read, which will be described later. Note that the position determining unit 1032 outputs the determination threshold to the area setting unit 107. In addition, the display processor 1031 outputs coordinate data of an area on the display screen of the display unit 102 and data used in the area setting unit 107, which correspond to the above-mentioned range, to the area setting unit 107.

The area setting unit 107 uses the setting data and the like stored in the first data storage unit 104 and data output from the document data processor 103 to generate data of a first determination area and a second determination area described later, and stores the data in the third data storage unit 108. Note that the area setting unit 107 also stores a threshold for lines other than the last line, and the determination threshold for determining whether the last line has been read, which is received from the position determining unit 1032, in the third data storage unit 108.

For example, in response to an instruction from the input unit 109, the determination unit 106 determines whether the text in the first determination area, stored in the third data storage unit 108, has been read, on the basis of the coordinates of the gaze position, stored in the second data storage unit 105, and stores the determination result in the third data storage unit 108. There are cases in which the determination unit 106 additionally outputs the determination result to the display unit 102. In addition, the determination performed by the determination unit 106 includes whether the text has been read to the end (has been finished reading).

Figure 4:
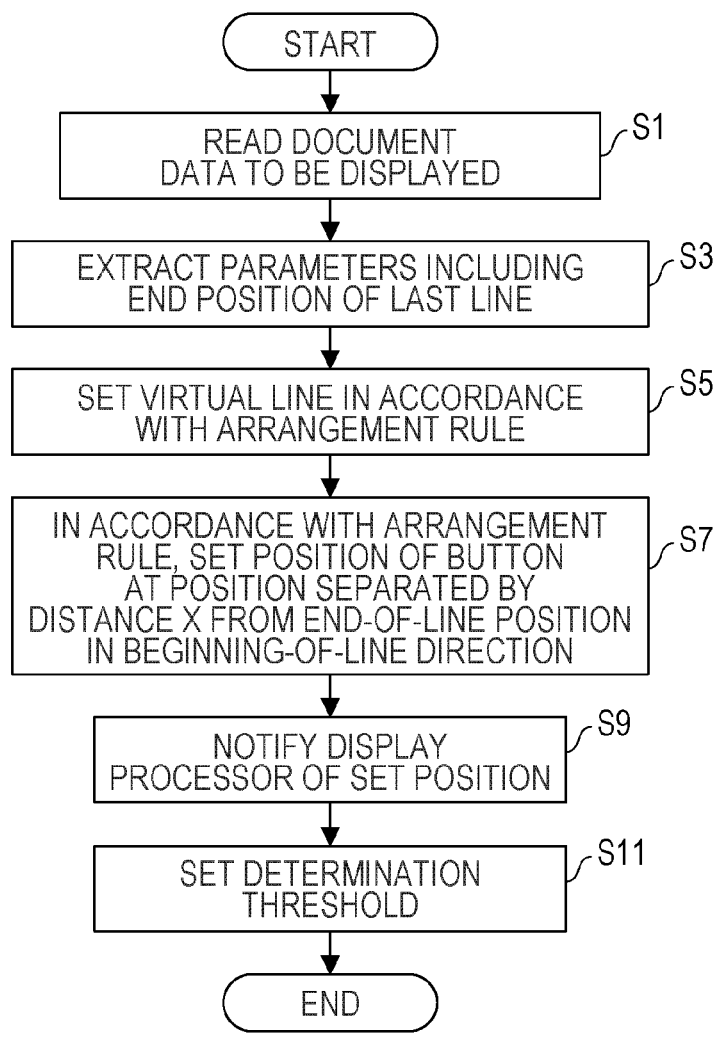
FIG. 4 is a flowchart of a process according to a first embodiment.

Next, for example, in response to an instruction from the input unit 109, a process performed by the document data processor 103 to display document data stored in the first data storage unit 104 will be described using FIG. 4.

For example, in response to an instruction from the input unit 109, the position determining unit 1032 of the document data processor 103 reads document data stored in the first data storage unit 104 (step S1). The position determining unit 1032 extracts, from the document data, parameters including the end-of-line position of the last line of text included in the document (step S3).

Figure 5:
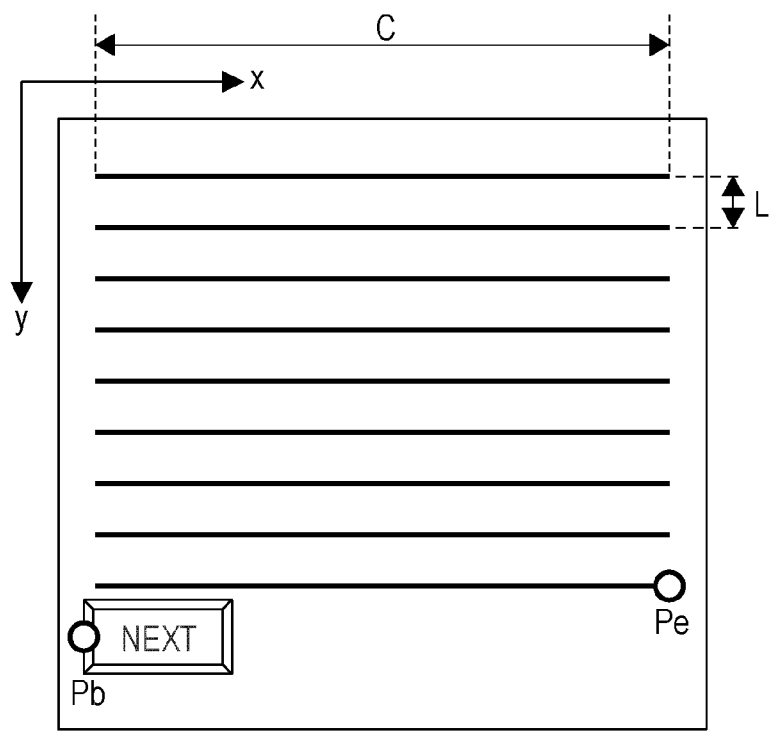
FIG. 5 is a diagram illustrating an example of document data processed in the first embodiment.

This embodiment assumes, for example, the case in which document data such as that illustrated in FIG. 5 is displayed. In the example illustrated in FIG. 5, the document includes only text, which includes nine lines written from left to right (which are simplified using solid lines). The horizontal length of one line is C, and the line spacing is L. It is assumed that the horizontal direction is represented by an x coordinate, and the vertical direction is represented by a y coordinate. In this embodiment, it is assumed that the end of the ninth line (that is, the end of the text) reaches the right end. Note that, for the sake of convenience of illustration, the button "next" is already illustrated. However, at this moment, the position of the button "next" is not established yet. It is assumed that the position of the left end of the button is represented by $Pb=(x_b, y_b)$.

In this step, the end-of-line position of the last line $Pe=(x_e, y_e)$ is extracted, and the line spacing L is extracted. In determination of the end-of-line position, if the end of the line is a symbol such as a period or a comma, the end of the line may be determined without including such symbols.

The position determining unit 1032 sets a virtual line below the last line in accordance with a button arrangement rule included in setting data stored in the first data storage unit 104, and sets the coordinates of the button on this line (step S5).

For example, if the button arrangement rule is a rule that arranges a button one line below the last line, $y_b=y_e+L$ is set. Note that the rule may be one that arranges a button two lines below the last line. In that case, $y_b=y_e+2L$ is set.

Further, in accordance with the button arrangement rule, the position determining unit 1032 sets the position of the button at a position separated by a distance X from the end-of-line position in a beginning-of-line direction (step S7).

Figure 6:
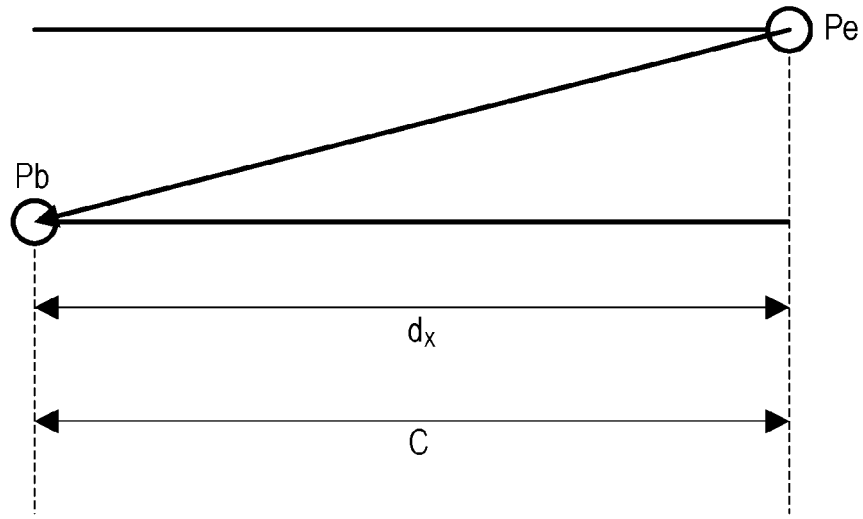
FIG. 6 is a diagram for describing an arrangement rule according to the first embodiment.

The arrangement rule includes a rule that, for example, as illustrated in FIG. 6, how far the button to be arranged is to be separated from the end Pe of the last line in a direction opposite to the text reading direction. In the example illustrated in FIG. 6, a distance $d_x$ that is a distance in the x-axis direction and that is the same as the line length C is set. Note that the distance $d_x$ is not limited to the line length C and may be set to an arbitrary length.

Figure 7:
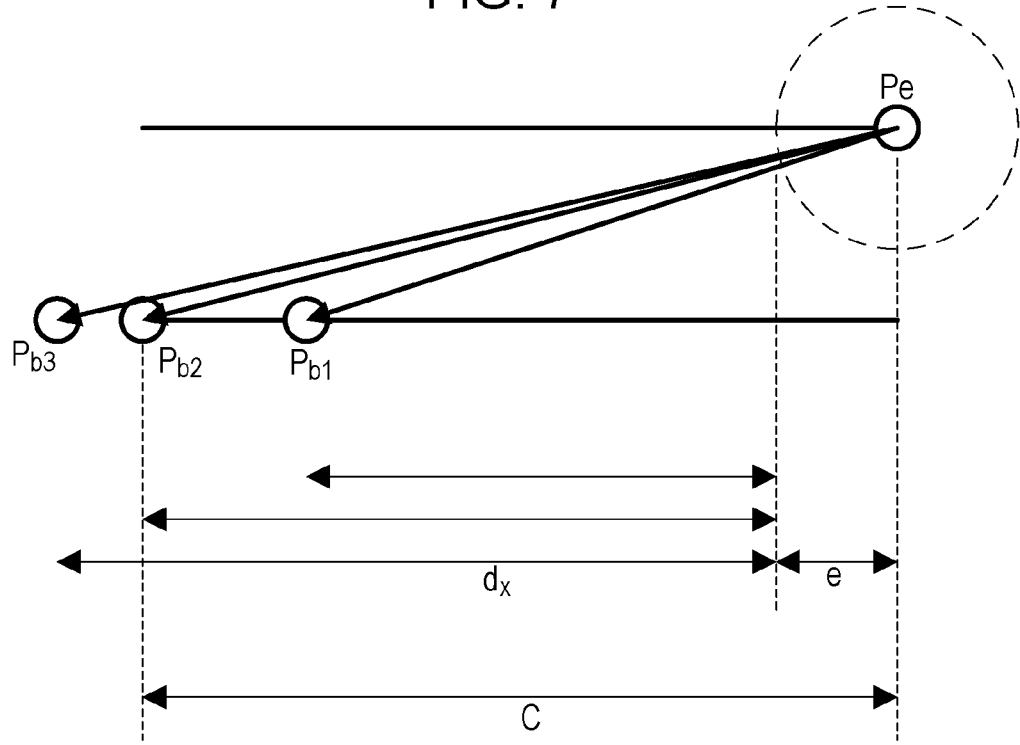
FIG. 7 is a diagram illustrating a modification of the arrangement rule according to the first embodiment.

Note that, as schematically illustrated in FIG. 7, in the case where the gaze position is detected at the end Pe of the last line, the actual gaze position is present within a gaze detection error circle with a radius e. That is, even when the gaze position is detected at the end Pe of the last line, the x-coordinate value of the actual gaze position may be $x_e-e$. Such a case is taken into consideration, and the result $d_x+e$ of adding a gaze detection error e to the specified distance $d_x$ may be adopted as the distance X. FIG. 7 illustrates three examples of d, and the button's positions $P_{b1}$, $P_{b2}$, and $P_{b3}$ are illustrated. Since the position $P_{b3}$ is on the left side of the beginning-of-line position, if the position $P_{b3}$ is beyond a display range, the button is undisplayable. Therefore, the distance $d_x$ which makes it impossible to display the button is not specifiable. In addition, if the distance $d_x$ is too short, the possibility of a detection error becomes higher. Thus, it is preferable that the distance X be close to C.

Figure 8:
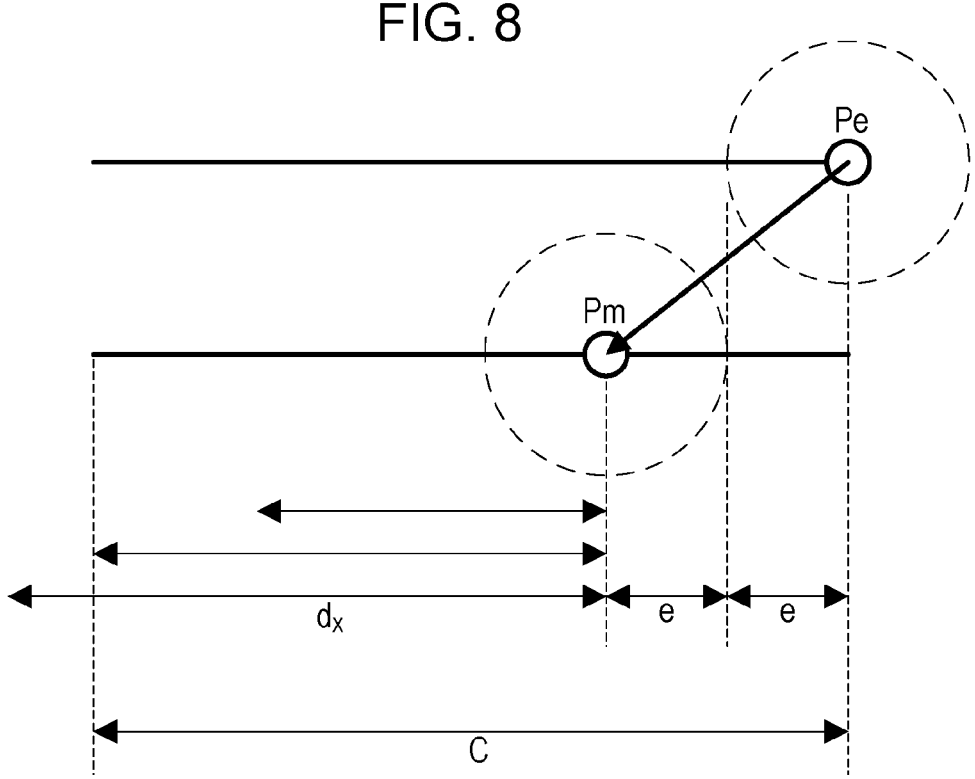
FIG. 8 is a diagram illustrating a modification of the arrangement rule according to the first embodiment.

Further, not only a gaze position detection error at the end Pe of the last line, but also a gaze position detection error after movement may be taken into consideration. As schematically illustrated in FIG. 8, at a gaze position Pm after movement, the actual gaze position Pm is present within a gaze detection error circle with the radius e. Note that the radius e indicating a gaze detection error may be changed in accordance with the gaze position, such that, for example, the radius e may be made smaller in a screen central portion and may be made greater toward a screen peripheral portion. That is, the movement distance of the gaze may be detected to be shorter by a length of 2e at maximum in the x-axis direction. Therefore, the result $d_x+2e$ of adding twice the gaze detection error e to the specified distance $d_x$ may be adopted as the distance X.

FIG. 8 also illustrates three examples of $d_x$. However, if the distance $d_x$ is beyond the display range, the button is undisplayable. Therefore, the distance $d_x$ which makes it impossible to display the button is not specifiable. In addition, if the distance $d_x$ is too short, the possibility of a detection error becomes higher. Thus, it is preferable that the distance X be close to C.

When the distance X is determined by any of the above-mentioned methods, the x-coordinate value of the button is calculated by $x_b=x_e-X$.

Thereafter, the position determining unit 1032 notifies the display processor 1031 of the set position data (step S9). A process performed by the display processor 1031 will be described later.

Further, the position determining unit 1032 calculates a determination threshold for determining whether the last line has been read, and outputs the determination threshold to the area setting unit 107 (step S11).

Figure 9:
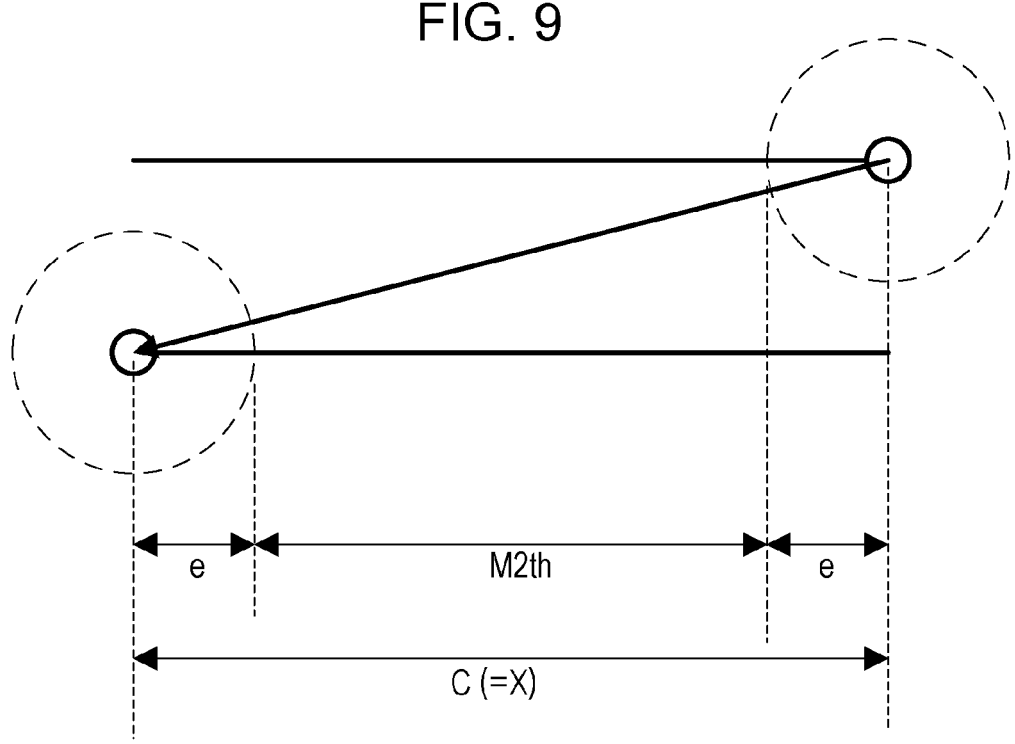
FIG. 9 is a diagram for describing a determination threshold according to the first embodiment.

In this embodiment, for example, the following determination threshold is set. That is, in a first example like that illustrated in FIG. 9, the gaze detection error e of the gaze position before the movement and the gaze detection error e of the gaze position after the movement are taken into consideration, and X−2e, which is subtraction of 2e from X (C in this case), is adopted as a determination threshold M2th.

Figure 10:
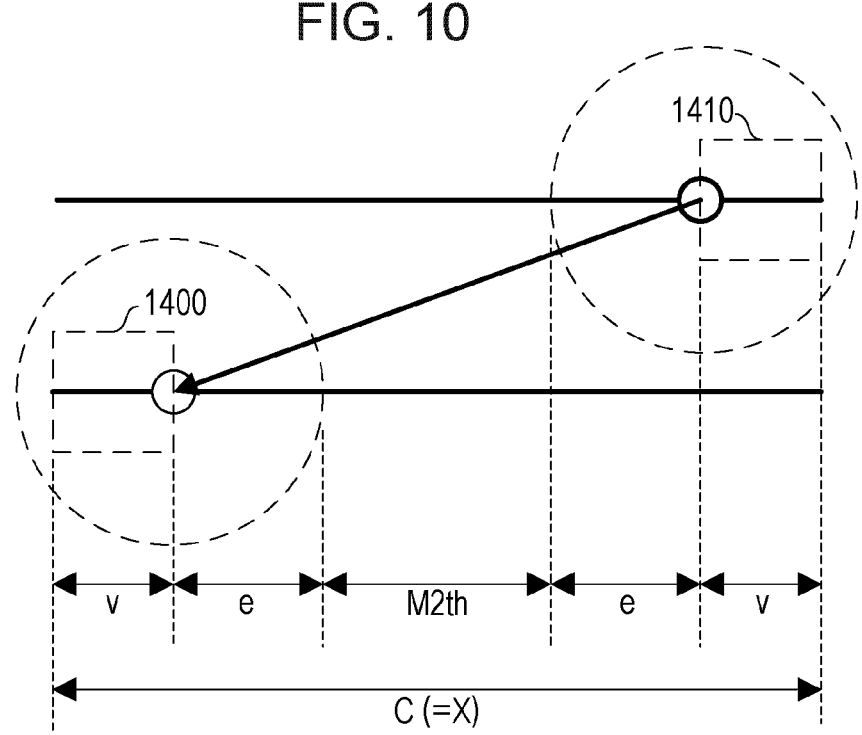
FIG. 10 is a diagram for describing the determination threshold according to the first embodiment.

Further, in a second example like that illustrated in FIG. 10, ranges 1400 and 1410 that are readable at one time are taken into consideration. That is, if the position of the button is within the range 1400 or 1410, which is readable at one time, it is possible to complete reading without moving the gaze to the end of a line, and the button is recognizable without moving the gaze to the beginning of a line. Therefore, in addition to the gaze detection error e of the gaze position before the movement and the gaze detection error e of the gaze position after the movement, the length v of each side of both the ranges 1400 and 1410 is taken into consideration, and X−(2e+2v), which is subtraction of 2e+2v from X (C in this case), is adopted as the determination threshold M2th.

Figure 11:
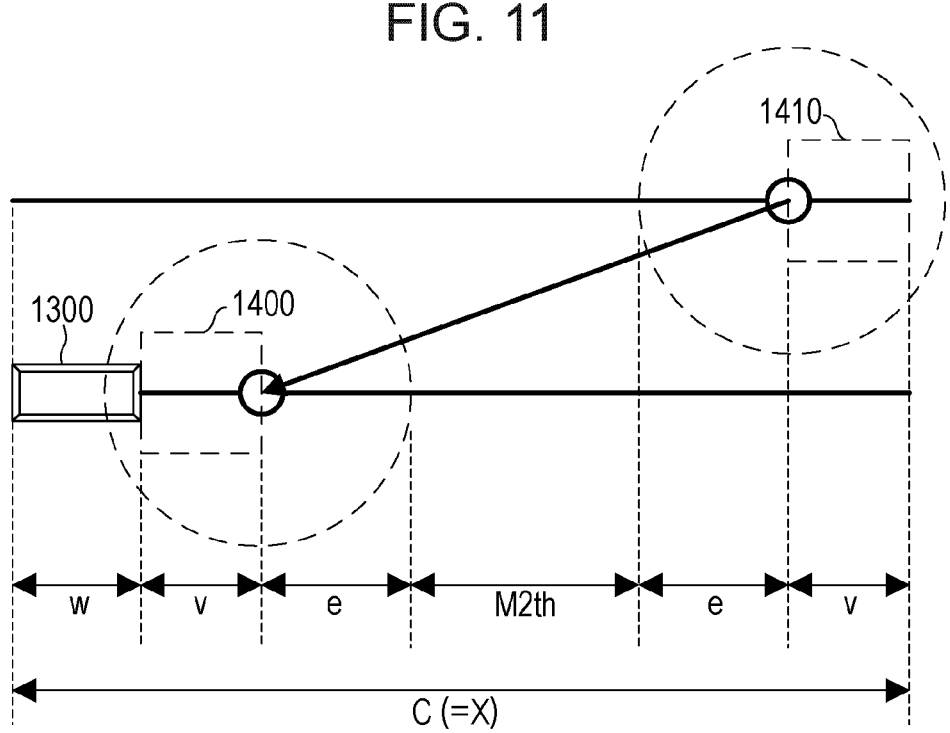
FIG. 11 is a diagram for describing the determination threshold according to the first embodiment.

Further, in a third example like that illustrated in FIG. 11, in addition to the second example, the length w of the button 1300 is also taken into consideration. That is, if the right end of the button 1300 is within the left end of the range 1400, which is readable at one time, the button 1300 is recognizable. Thus, X−(2e+2v+w) is adopted as the determination threshold M2th.

In accordance with any of the modes in these examples, the determination threshold M2th for the last line is calculated from X.

By executing the above-described process, it becomes possible to arrange the button 1300 at a position at which whether the text has been read to the last line is determinable. Further, it also becomes possible to calculate the determination threshold for the last line, which will be used in a process of determining whether text has been read, described alter.

In this embodiment, as has been described above, text in which the direction of reading is set to be from left to right is discussed by way of example. However, text in which the direction of reading is set to be from top to bottom is proccesable in the same manner by replacing left with top and right with bottom.

Next, a process of determining whether text has been read will be described using FIGS. 12 to 18.

Figure 12:
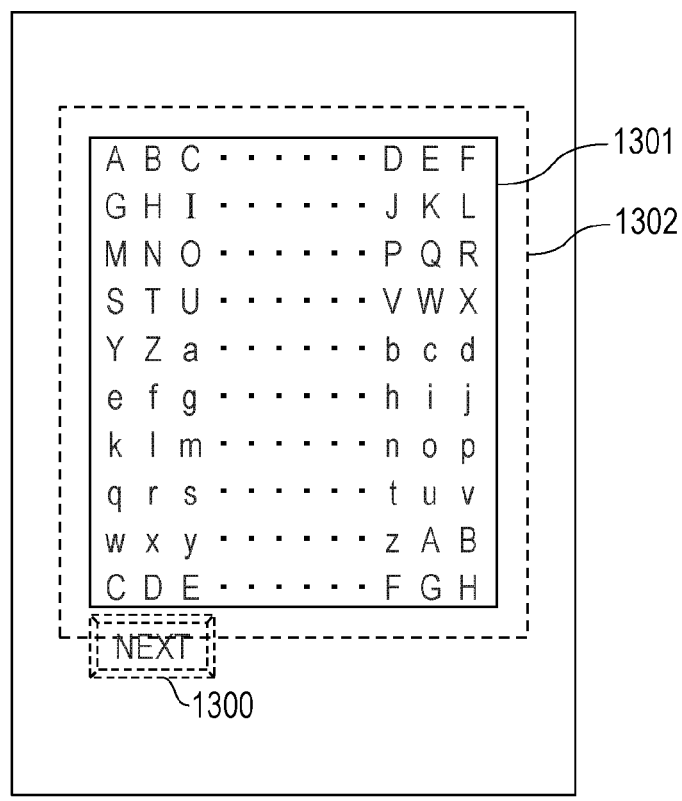
FIG. 12 is a diagram for describing determination areas.

First, using FIG. 12, determination areas used in a process of determining whether text has been read will be described. FIG. 12 illustrates an example of a display screen of the display unit 102. The display screen includes text, and the button 1300 for entering that the text has been read. In this embodiment, a range for determining whether text has been read is set in advance for that text. In the example illustrated in FIG. 12, text from "ABC" at the left end of the first line to "FGH" at the right end of the tenth line is stored as document data in the first data storage unit 104, and further, the range of this text is stored as range data. A rectangular (such as a minimum rectangular) area 1301 surrounding the text in this range is a first determination area. The display processor 1031 outputs data of coordinate data representing the first determination area (such as the coordinate values of the upper-right vertex and the lower-left vertex, or the coordinate values of the upper-left vertex and the lower-right vertex) and data used in a process performed by the area setting unit 107 (for example, when the direction of reading is set to be from left to right, the coordinate values of the left-end character and the right-end character) to the area setting unit 107. The area setting unit 107 sets, for the area 1301, an area 1302 as a second determination area on the basis of a gaze detection error included in setting data (an error (length in this case) of the coordinate values output by the gaze detector 101). In the case where the coordinates of the gaze position fall within this second determination area, the determination unit 106 determines whether gaze movement satisfies a condition(s) described later. Note that, in FIG. 12, the area 1302 is broader than the area 1301 and the area 1302 includes the area 1301. Alternatively, the area 1302 and the area 1301 may have the same range, or the area 1302 may not include the area 1301.

Figure 13:
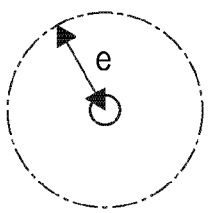
FIG. 13 is a diagram for describing a gaze detection error.
Figure 14:
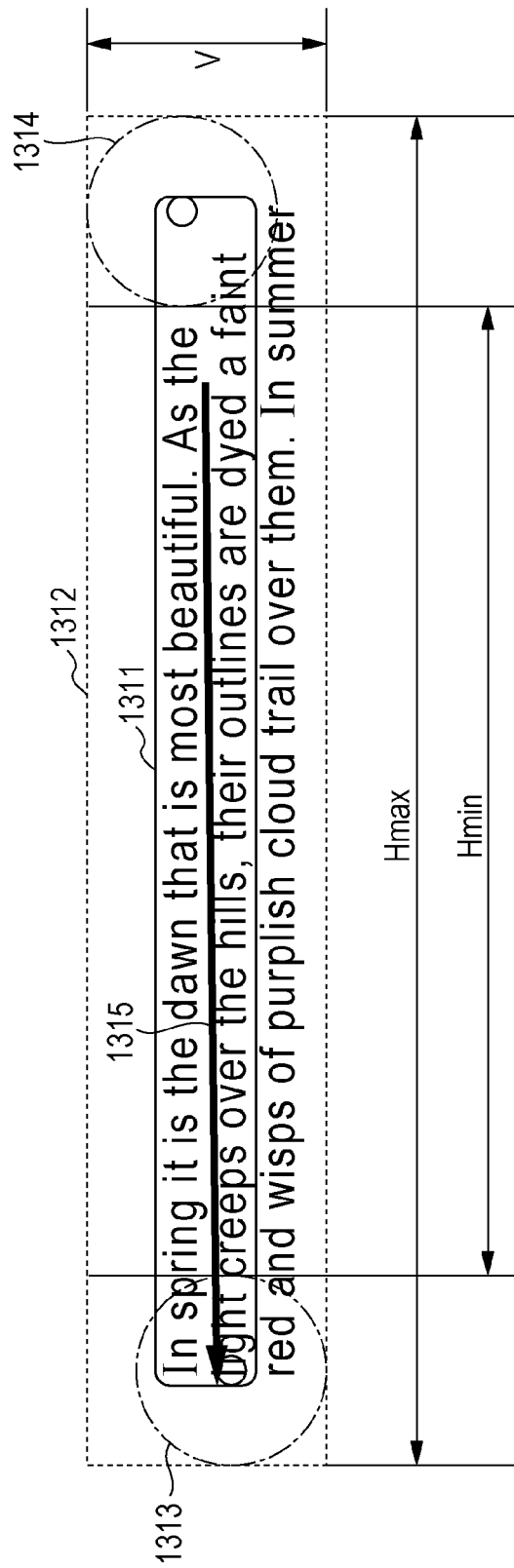
FIG. 14 is a diagram for describing the determination areas.

Next, a setting example of the second determination area will be described using FIGS. 13 and 14. In this setting example, a setting method using the above-mentioned gaze detection error e is adopted. When a user looks at a certain position, the coordinates of the position fall within a circle that is centered at the position and that has the radius e, as illustrated in FIG. 13. Therefore, as illustrated in FIG. 14, in the case where the true gaze position comes to the right-end character in a first determination area 1311, the coordinates of the gaze position from the gaze detector 101 may represent an arbitrary position in a circle 1314 with the radius e. Similarly, in the case where the true gaze position comes to the left-end character in the first determination area 1311, the coordinates of the gaze position from the gaze detector 101 may represent an arbitrary position in a circle 1313 with the radius e.

Therefore, the length Hmax from the left end of the circle 1313 to the right end of the circle 1314 is adopted as the horizontal length of the second determination area. If the left-end character were virtually moved to the bottom line while maintaining the coordinate in the horizontal direction and the right-end character were virtually moved to the top line while maintaining the coordinate in the horizontal direction (FIG. 14 is already in this state), a rectangle that circumscribes the circle 1313, which is centered at the center of the left-end character after the movement and which has the radius e, and the circle 1314, which is centered at the center of the right-end character after the movement and which has the radius e, is adopted as a second determination area 1312. Note that the four corners of the second determination area 1312 may be rounded by the arc with the radius e. In addition, the length V in the vertical direction of the second determination area 1312 is the length between the bottom end of the circle 1313, which is centered at the center of the left-end character after the movement and which has the radius e, and the top end of the circle 1314, which is centered at the center of the right-end character after the movement and which has the radius e.

In the case where the user finishes reading the right-end character of the first line and then continues reading the left-end character of the second line, the gaze detection error being taken into consideration, the gaze position moves by the length Hmin from the left end of the circle 1314 set at the right-end character of the first line to the right end of the circle 1313 set at the left-end character of the second line, which is the case of the shortest movement distance. In the case of the longest movement distance, the gaze position moves by the horizontal length Hmax of the second determination area 1312. That is, in the case of a newline, the coordinates of the gaze position move by Hmin to Hmax in a direction opposite to the direction of reading text in the first determination area (an arrow 1315 in FIG. 14). At any rate, in the case of a newline, the gaze position moves by Hmin at minimum in the second determination area 1312. This movement by Hmin at minimum of the gaze position is detected. Although a determination may be performed in the sense of Euclidean distance, if the reading direction is set to a positive direction of the x-axis or y-axis, for example, it may be confirmed that the difference between the x-coordinate value or the y-coordinate value of the position before the movement and the x-coordinate value or the y-coordinate value of the position after the movement is greater than or equal to the threshold Hmin.

Note that, to simplify the setting of the second determination area 1312, the boundary of the second determination area 1312 may be set to be outside of the boundary of the first determination area 1311 by the gaze detection error e.

In addition, the movement distance threshold may be set on the basis of a readable area representing a range that a user is able to read at one time. In this embodiment, it is assumed that, for the readable area, for example, data of an average user is stored as setting data in the first data storage unit 104.

Figure 15:
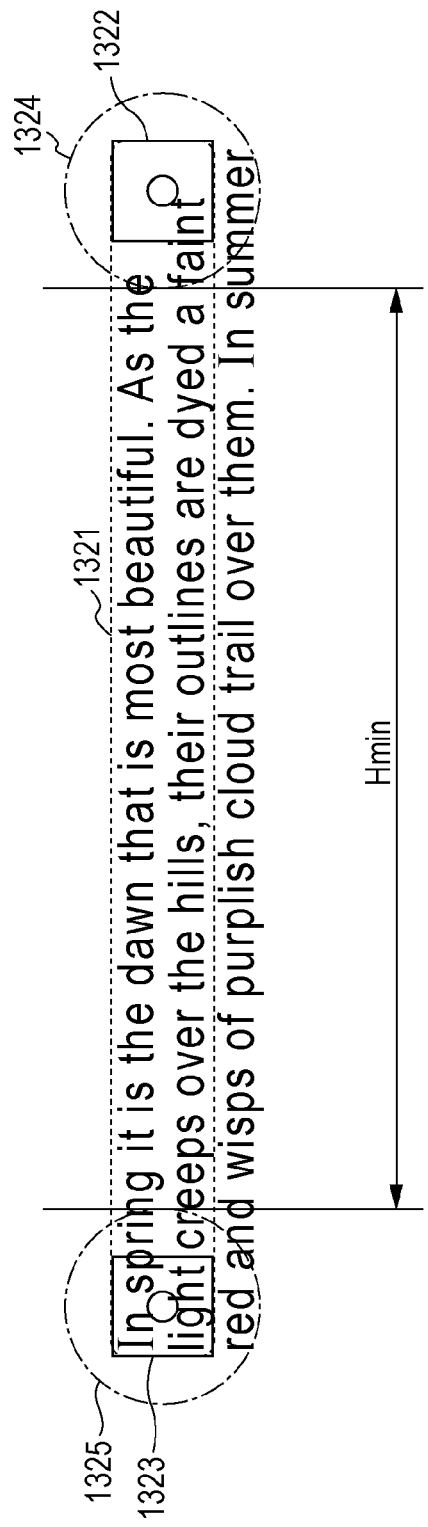
FIG. 15 is a diagram for describing the determination areas.

As illustrated in FIG. 15, the threshold Hmin may be set. That is, the right end of a readable area 1322 representing a range that a user is able to read at one time is arranged in agreement with the right end of a first determination area 1321, and a circle 1324 that has the gaze detection error e as a radius is centered at the center of the readable area 1322. Similarly, the left end of a readable area 1323 is arranged in agreement with the left end of the first determination area 1321, and a circle 1325 that has the gaze detection error e as a radius is centered at the center of the readable area 1323. The distance between the right end of the circle 1325 and the left end of the circle 1324 may be used as the distance threshold Hmin.

This is because of the following reason. That is, even when the gaze is not moved to the right-end character, if the gaze is moved such that a readable area includes the right-end character, text is readable to the right-end character. Similarly, even when the gaze is not moved to the left-end character, if the gaze is moved such that a readable area includes the left-end character, text is readable to the left-end character.

Next, FIG. 16 illustrates an example of data stored in the third data storage unit 108. In the example illustrated in FIG. 16, the data includes a time, such as a determination start time or a determination end time, coordinate data defining the range of the first determination area (such as the upper left and lower right coordinate values), coordinate data defining the range of the second determination area (such as the upper right and lower left coordinate values), the movement distance threshold, the number of lines of text included in the first determination area, and a determination flag indicating whether text has been read. In this embodiment, the movement distance threshold is different for the last line and the other lines. Therefore, as the movement distance threshold, lines other than the last line (nine lines) and the last line (one line) are registered. For the number of lines, the number of lines of lines other than the last line and the number of lines of the last line are registered. For the determination flag, a flag for lines other than the last line and a flag for the last line are prepared.

For the number of lines of text included in the first determination area, the number of lines may be included in text data in the first data storage unit 104, or, if the number of lines changes according to display, the number of displayed lines is identified by the display processor 1031 or the like.

Figure 17:
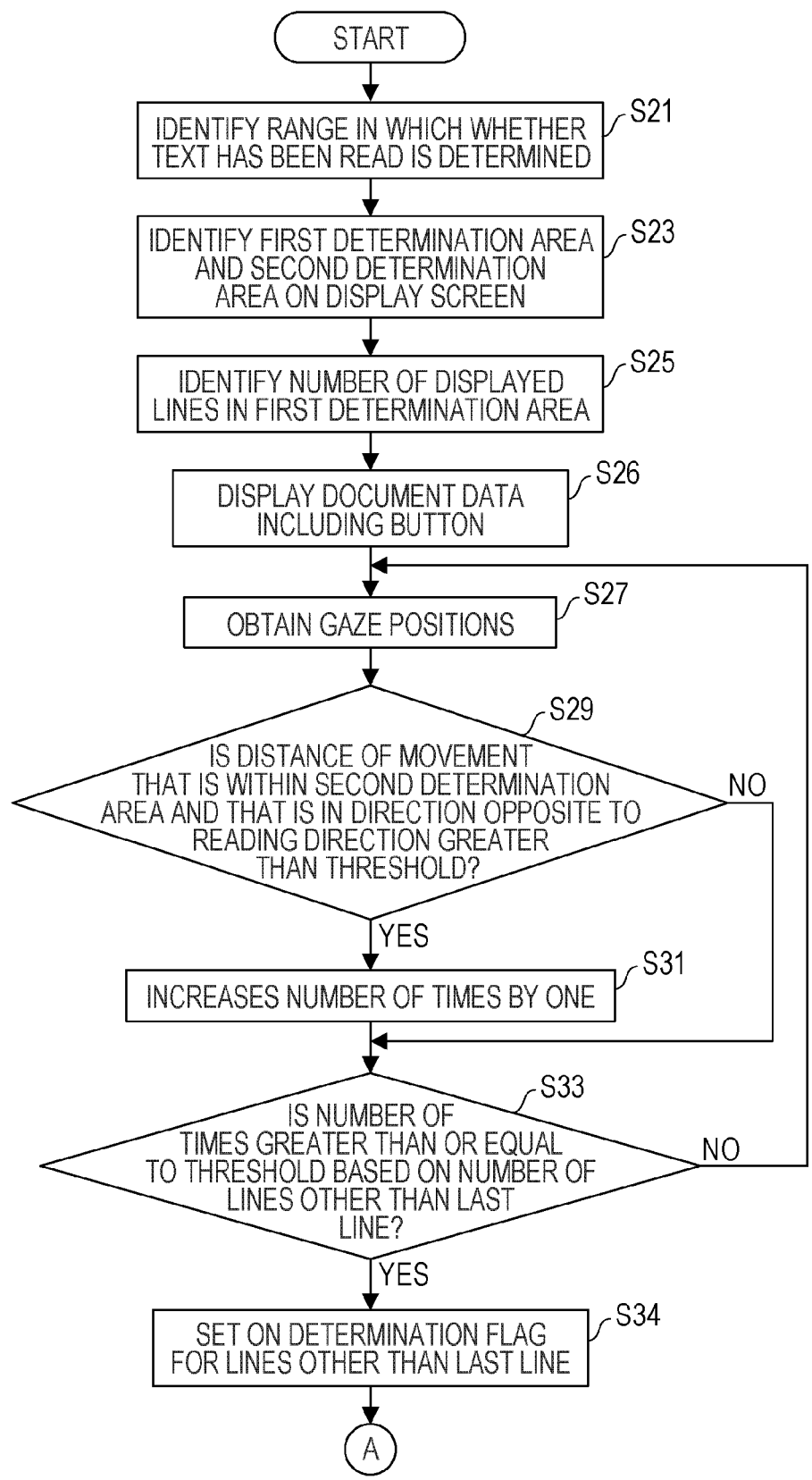
FIG. 17 is a flowchart illustrating a process of determining whether text has been read.

Next, the details of a process performed by the information processing apparatus 100 according to this embodiment will be described using FIGS. 17 and 18.

For example, in response to an instruction from the input unit 109 or the like, the display processor 1031 reads document data from the first data storage unit 104. The display processor 1031 identifies a range in which whether text included in the document has been read is determined, from range data or the like stored in the first data storage unit 104 (step S21 in FIG. 17). The display processor 1031 identifies coordinate data of a first determination area on the display screen of the display unit 102, and outputs the coordinate data to the area setting unit 107. In addition, the area setting unit 107 sets a second determination area so as to include the first determination area, taking into consideration a gaze detection error, and stores the coordinate data of the first determination area and the coordinate data of the second determination area in the third data storage unit 108 (step S23). A process performed by the area setting unit 107 is like a process described using FIG. 14. In addition, in this process, as illustrated in FIG. 14 or 15, the area setting unit 107 calculates a movement distance threshold Hmin (Mth in the example illustrated in FIG. 16) for lines other than the last line, and stores the threshold Hmin along with the determination threshold M2th for the last line, obtained from the position determining unit 1032, in the third data storage unit 108.

In addition, the area setting unit 107 obtains data of the number of lines on the display screen (the number of lines in the reading direction; hereinafter referred to as "the number of displayed lines") from the display processor 1031, or, in the case where the number of displayed lines is fixed, reads data of the number of displayed lines from the first data storage unit 104, and stores the data in the third data storage unit 108 (step S25). In this step, the number of displayed lines is separately stored for the last line and lines other than the last line in the third data storage unit 108.

The display processor 1031 displays the document data in which the button is arranged at the position received from the position determining unit 1032, on the display screen of the display unit 102 (step S26). In addition, the gaze detector 101 detects the coordinates of the gaze position, and stores the coordinates in the second data storage unit 105.

The determination unit 106 reads the data of the coordinates of the newest gaze position and the coordinates of the gaze position one unit time ago, which are stored in the second data storage unit 105 (step S27). Accordingly, the positions before and after the movement are identified on the display screen, thereby calculating the movement distance. Note that, in this embodiment, the movement distance may be the difference between coordinate values in an axis direction parallel to the reading direction, or Euclidean distance may be adopted.

On the basis of the coordinate data of the second determination area, stored in the third data storage unit 108, the determination unit 106 determines whether the distance of movement whose positions before and after the movement are within the second determination area and that is in a direction opposite to the text reading direction in the first determination area is greater than or equal to the threshold Hmin (Mth in the example illustrated in FIG. 16) (step S29). That is, whether a line break has occurred is determined.

In the case where the positions before and after the movement are not within the second determination area or the distance of the movement in a direction opposite to the text reading direction in the first determination area is not greater than or equal to the threshold Hmin, the occurrence of a line break is not determined. The process proceeds to step S33.

In contrast, in the case where the positions before and after the movement are within the second determination area, and the distance of the movement in a direction opposite to the text reading direction in the first determination area is greater than or equal to the threshold Hmin, the occurrence of a line break is determined. The determination unit 106 increases the number of times a line break is detected by one (step S31).

Then, the determination unit 106 determines whether the number of times a line break is detected is greater than or equal to a threshold based on the number of lines other than the last line (step S33). In this embodiment, the threshold is the same as the number of lines. In the case where the number of times a line break is detected is not greater than or equal to the threshold based on the number of lines other than the last line, the process returns to step S27. In contrast, in the case where the number of times a line break is detected is greater than or equal to the threshold based on the number of lines other than the last line, the determination unit 106 sets "on" the determination flag for lines other than the last line in the third data storage unit 108 (step S34). Then, the process proceeds to a process illustrated in FIG. 18 via a terminal A.

The determination unit 106 reads data of the coordinates of the newest gaze position and the coordinates of the gaze position one unit time ago, which are stored in the second data storage unit 105 (step S35). Then, the determination unit 106 determines whether the movement distance in a certain direction (a direction opposite to the text reading direction in the first determination area in this embodiment) is greater than or equal to the determination threshold M2th for the last line (step S37). That is, whether gaze movement to the button has occurred is determined. In this embodiment, this step is also determined on the basis of the difference between the x-coordinate values. If a too great movement distance is obtained, such a distance may be ignored.

For example, if the movement distance in the certain direction is not greater than or equal to the determination threshold M2th for the last line, the determination unit 106 instructs the display processor 1031 to display a message indicating that there is unread text, for example, on the display unit 102 (step S38). Then, the process ends. For example, the button may be made unclickable.

In contrast, if the movement distance in the certain direction is greater than or equal to the determination threshold M2th for the last line, the determination unit 106 sets "on" the determination flag for the last line of this text in the third data storage unit 108 (step S39). Then, the process ends. In accordance with step S39, the button may be made clickable. That is, although the button may be displayed in step S26, the button may be made unclickable; only when it has been determined that the text has been read to the last line, the button may be made clickable. Note that display that guides the user toward the button may be performed in step S34.

By performing the above-described process, even when the gaze detector 101, which is of low accuracy, is used, it is possible to confirm whether text has been read to the end.

Second Embodiment

In the first embodiment, the end of the last line of displayed text is at the right end of the line. Therefore, it is easy to arrange a button for entering that text has been read on the left side so as to be within the display range. In such a case, as with the case of lines other than the last line, the last line may be subjected to detection of a newline (that is, a line break) in a direction opposite to the reading direction, and this only has a small effect on a process of determining whether text has been read.

However, the end of the last line may come to a position other than the right end. Even in such a case, there will be no problem when the button is arranged on the left side so as to be within the display range. However, in some cases, it is impossible to arrange the button at such a position. In this embodiment, a process for handling such a case will be described.

Figure 19:
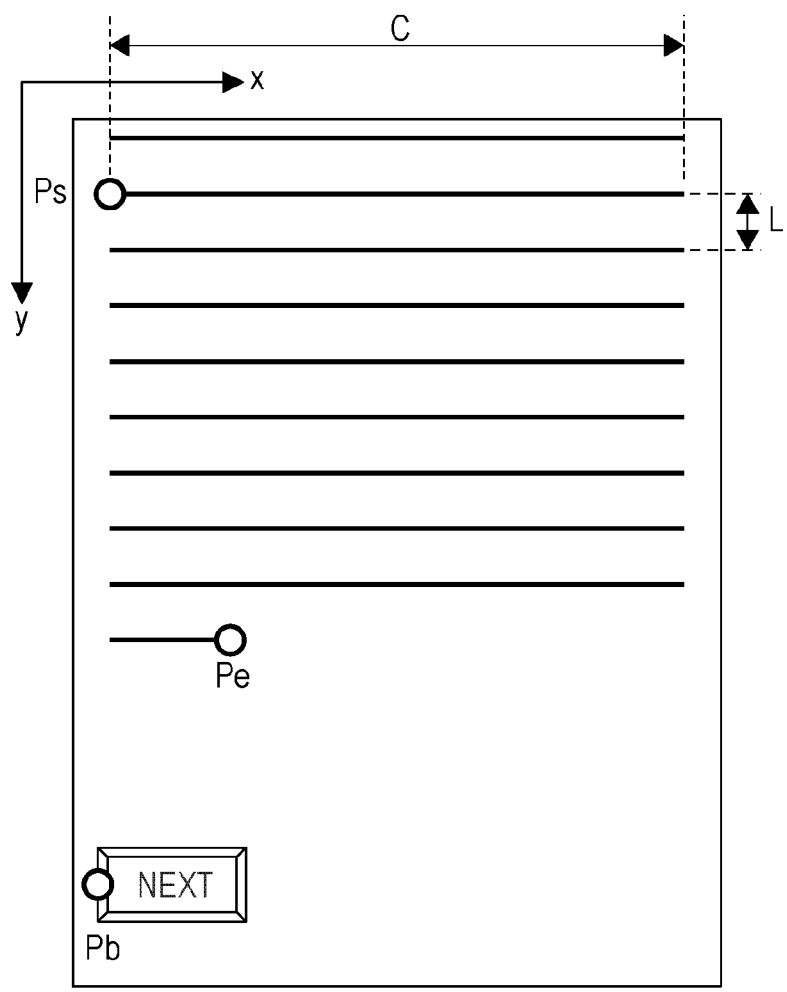
FIG. 19 is a diagram illustrating an example of document data processed in a second embodiment.

For example, in the case of a document like that illustrated in FIG. 19, the line spacing L and the maximum line length C are the same as those in the first embodiment; however, the end position Pe of the last line is not at the right end of the line, but is relatively on the left side. In such a case, it may be difficult in some cases to arrange the button on the further left in terms of the detection of the gaze movement. Therefore, in this embodiment, as illustrated in FIG. 19, the button is arranged a certain length below the last line, thereby facilitating the detection of the gaze movement from the end of the last line to the button. Also in this embodiment, it is assumed that the left end of the button is set as the button position Pb.

Figure 20:
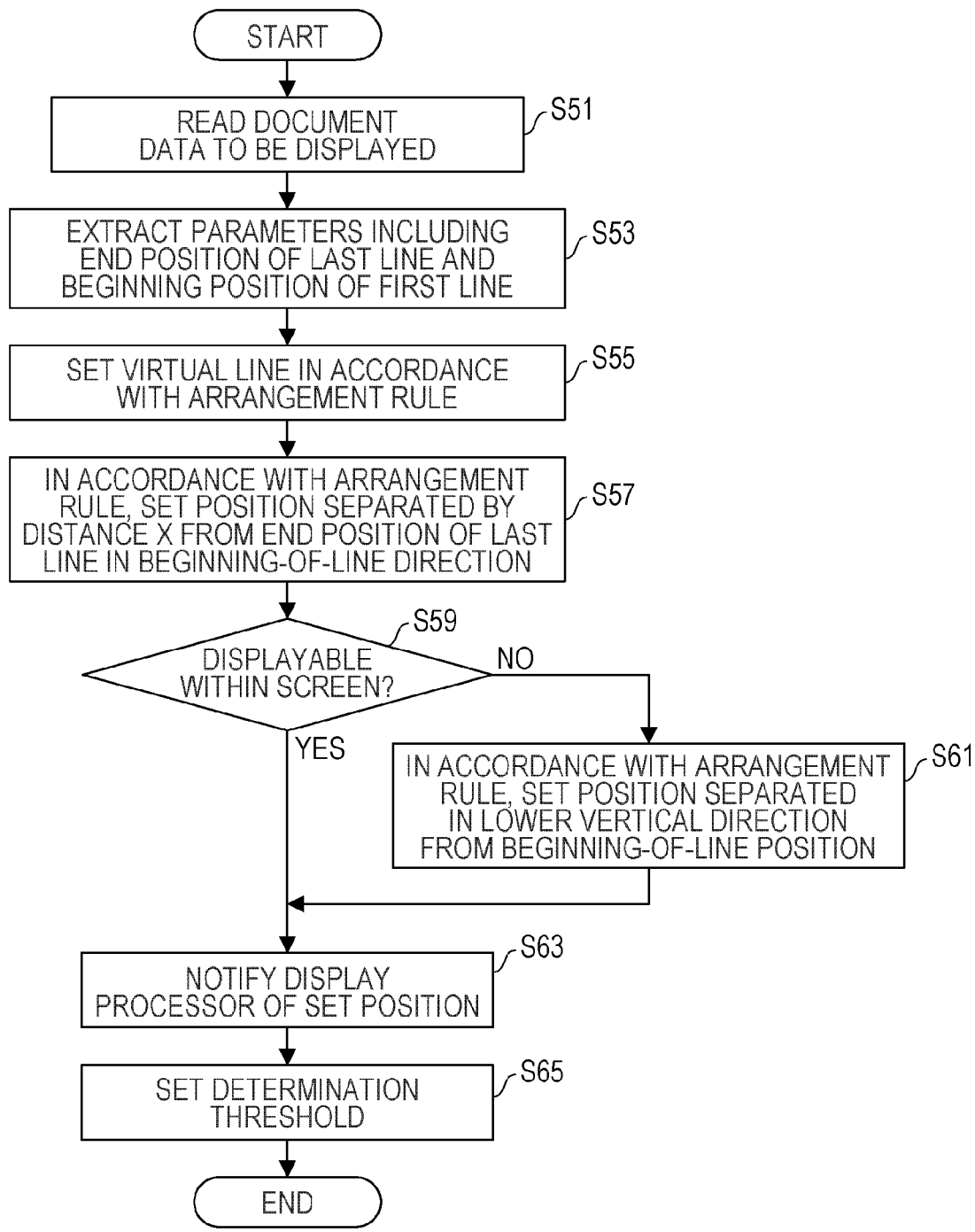
FIG. 20 is a flowchart of a process according to the second embodiment.

For example, in response to an instruction from the input unit 109, the position determining unit 1032 of the document data processor 103 reads document data stored in the first data storage unit 104 (step S51 in FIG. 20). The position determining unit 1032 extracts, from the document data, parameters including the end-of-line position of the last line and the beginning-of-line position of the first line of text included in the document (step S53).

This embodiment assumes the case in which document data such as that illustrated in FIG. 19 described above is displayed. As in FIG. 5, the document includes only text, which includes nine lines written from left to right (which are simplified using solid lines), and it is assumed that the horizontal direction is represented by an x coordinate, and the vertical direction is represented by a y coordinate. In this embodiment, it is assumed that the end of the ninth line (that is, the end of the text) is not at the right end, but is within an x coordinate value of 0 and C. Note that, for the sake of convenience of illustration, the button "next" is already illustrated. However, at this moment, the position of the button "next" is not established yet. It is assumed that the position of the left end of the button is represented by $Pb=(x_b, y_b)$. Further, the position of the beginning of the text, that is, the position of the beginning of the first line $Ps=(x_s, y_s)$, is also extracted. Similarly, the line spacing L is also extracted.

The position determining unit 1032 sets a virtual line below the last line in accordance with a button arrangement rule included in setting data stored in the first data storage unit 104, and sets the coordinates of the button on this line (step S55).

For example, if the button arrangement rule is a rule that arranges a button one line below the last line, $y_b=y_e+L$ is set. Note that the rule may be one that arranges a button two lines below the last line. In that case, $y_b=y_e+2L$ is set.

Further, in accordance with the button arrangement rule, the position determining unit 1032 sets the position of the button at a position separated by a distance X from the end-of-line position toward the beginning-of-line position (step S57).

The arrangement rule includes a rule that, for example, as in the first embodiment, how far the button to be arranged is to be separated from the end Pe of the last line in a direction opposite to the text reading direction. In this embodiment, it is assumed that a distance that is in the x-axis direction and that is eighty percent of the line length C, that is, a distance $d_x=0.8C$, is specified. Note that eighty percent is only one example, and, as in the first embodiment, there may be cases in which $X=d_x$, $X=d_x+e$, or $X=d_x+2e$.

Once the distance X is determined as above, the x coordinate value of the button is calculated by $x_b=x_e-X$.

Thereafter, the position determining unit 1032 determines whether the set position is a position displayable within the display screen of the display unit 102 (step S59). For example, when the origin of the coordinates of the display range is (0, 0), if the x coordinate value or the y coordinate value becomes a negative value, it is determined that the position is out of the display range. In this process flow so far, the x coordinate value may become a negative value.

If the set position is a displayable position, the process proceeds to step S63. In contrast, if the set position is not a displayable position, the position determining unit 1032 sets a position separated in a lower vertical direction from the beginning position of the last line in accordance with the button arrangement rule (step S61).

Figure 21:
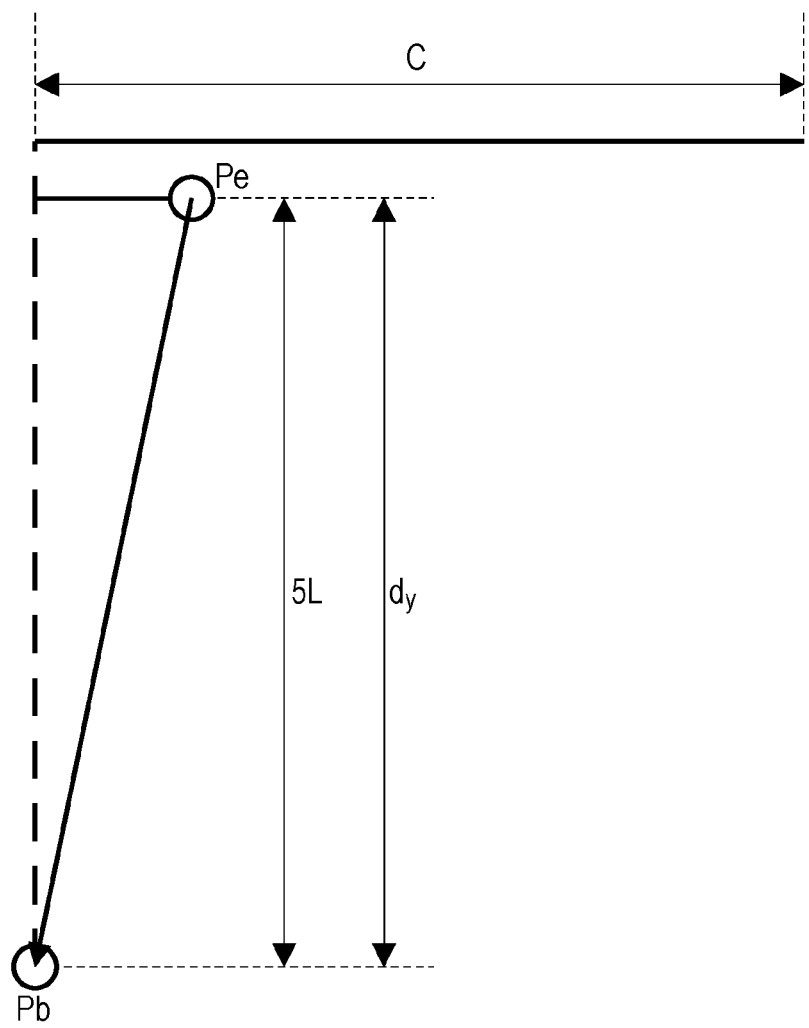
FIG. 21 is a diagram for describing button arrangement according to the second embodiment.

For example, if there is a rule that $d_y=5L$, as illustrated in FIG. 21, $y_b=y_e+5L$ is set, and $x_b=x$, is set. Note that $d_y=5L$ is only one example, and, for example, the rule may be $d_y=C$. The rule may be any rule with which it is possible to detect the gaze movement in a lower vertical direction that does not generally occur when reading text.

Figure 22:
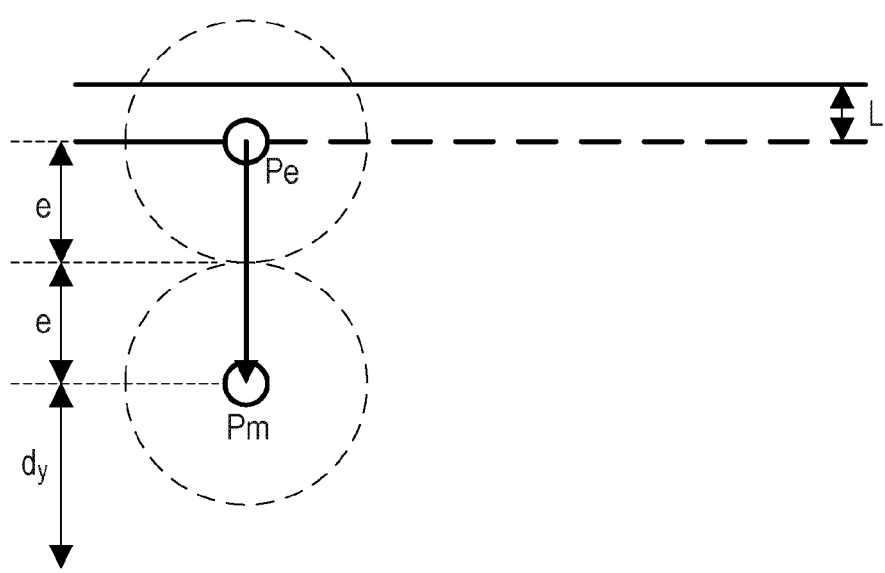
FIG. 22 is a diagram for describing the button arrangement according to the second embodiment.

In addition, as in the first embodiment, a gaze detection error may be taken into consideration. There are cases in which, as illustrated in FIG. 7, a gaze detection error at the end position of the last line is taken into consideration, or, in addition to a gaze detection error at the end position of the last line, a gaze detection error after the movement may also be taken into consideration, as illustrated in FIG. 22, and $y_b=d_y+2e$ may be set in order to ensure that the gaze moves by $d_y$.

Figure 23:
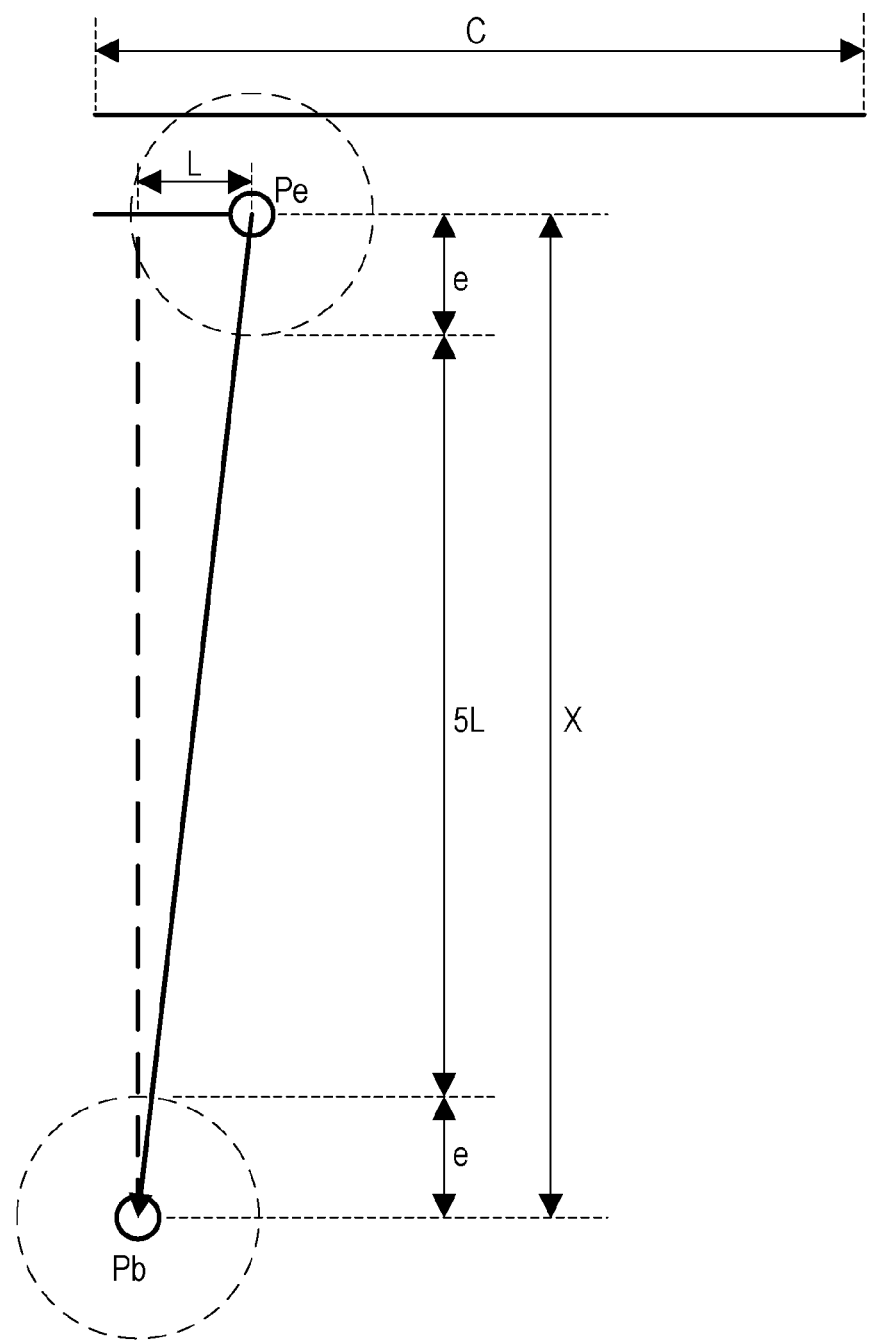
FIG. 23 is a diagram for describing the button arrangement according to the second embodiment.

That is, in order to reliably cause the gaze movement such as $d_y=5L$ or C to occur, as illustrated in FIG. 23, $y_b=y_e+(5L+2e)$ is set.

Note that, for $x_b$, $x_e$ may be used instead of $x_s$. As illustrated in FIG. 23, an arrangement that causes the gaze to be moved in such a manner that a newline in the first embodiment is rotated by 90 degrees, such as $x_e-L$, may be adopted.

Thereafter, the position determining unit 1032 notifies the display processor 1031 of the set position data (step S63). Since a process performed by the display processor 1031 is the same as or similar to that in the first embodiment, a description thereof is omitted.

Further, the position determining unit 1032 calculates a determination threshold for determining whether the last line has been read, and outputs the determination threshold to the area setting unit 107 (step S65).

Also in this embodiment, in the case where the positions set in step S55 and S57 are adopted, a process that is the same as or similar to that in the first embodiment is performed.

Figure 24:
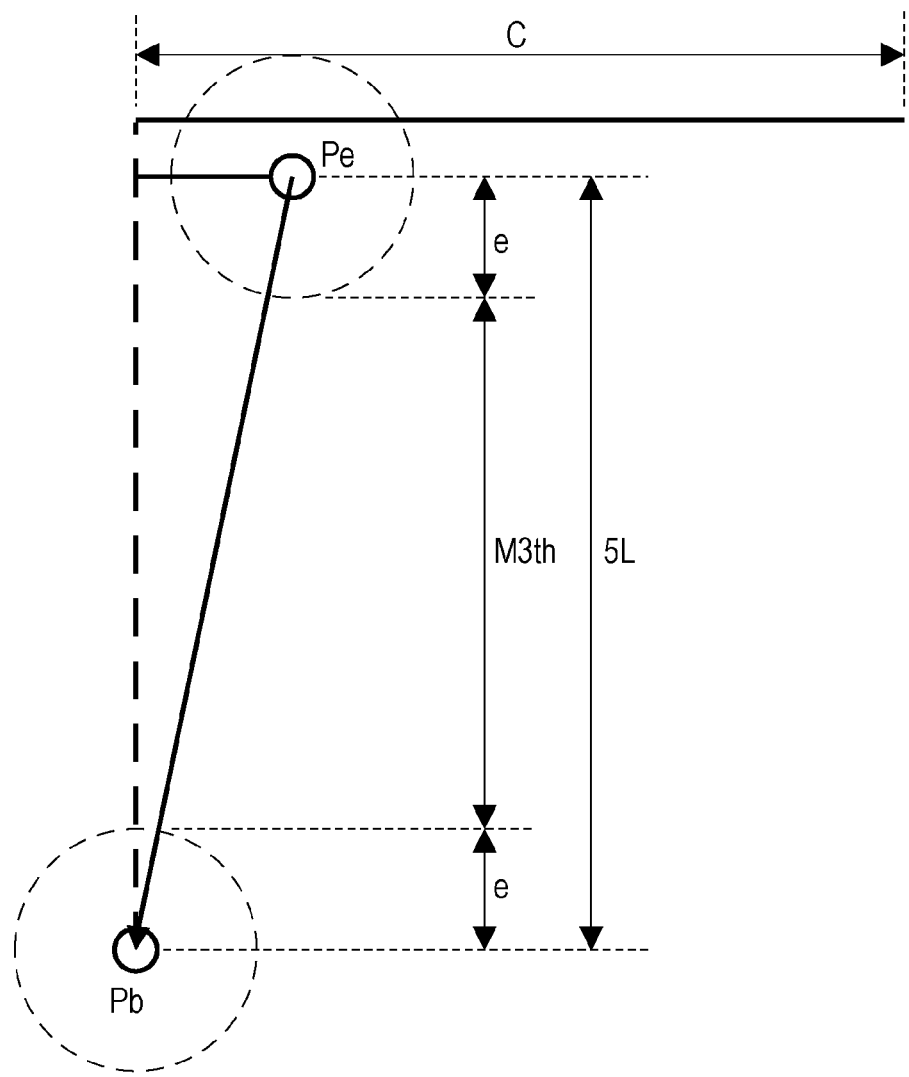
FIG. 24 is a diagram for describing a determination threshold according to the second embodiment.

In addition, in the case where the position set in step S61 is used, for example, the following determination threshold is set. That is, in an example illustrated in FIG. 24, the gaze detection error e of the gaze position before the movement and the gaze detection error e of the gaze position after the movement are taken into consideration, and X−2e, which is subtraction of 2e from X (5L in this case), is adopted as a determination threshold M3th. Note that, since the movement direction is different, data of the movement direction (y-axis direction in this case) is also added to the determination threshold M3th, and the data is output to the area setting unit 107.

Figure 18:
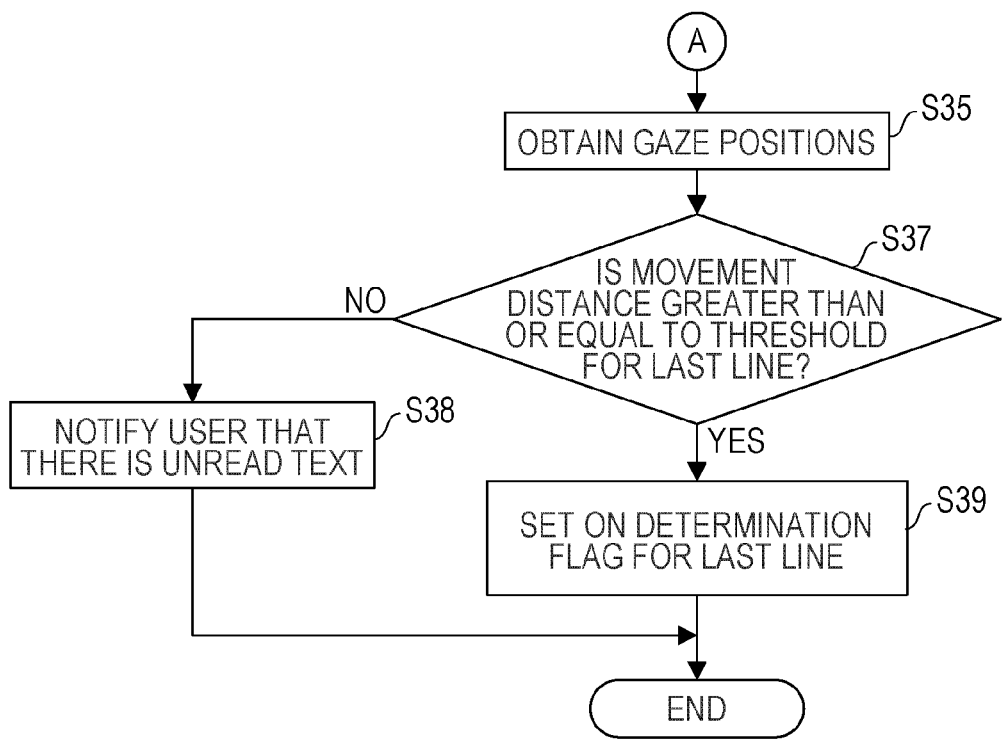
FIG. 18 is a flowchart illustrating the process of determining whether text has been read.

Therefore, in step S37 in the process flow illustrated in FIG. 18, the determination unit 106 determines whether the movement distance in a certain direction, that is, a direction orthogonal to the reading direction (more specifically, a direction that is a direction from the first line to the last line and that is orthogonal to the reading direction) is greater than or equal to the determination threshold M3th for the last line.

Also in such a case, the determination threshold M3th may be set by taking into consideration a range that is readable at one time.

By executing the above-described process, the button position is changed in accordance with the end position of the last line to a position at which whether the text has been read to the last line is determinable, and it becomes possible to arrange the button at that position. Further, it also becomes possible to calculate the determination threshold for the last line, which is used in the above-described process of determining whether text has been read.

Third Embodiment

In the second embodiment, the example has been described in which, in text whose reading direction is from left to right, the button is arranged in a lower vertical direction, thereby making it possible to detect the characteristic gaze movement representing that the last line has been read. However, there are cases in which there is not much space in a lower vertical direction. In addition, the characteristic gaze movement representing that the last line has been read is not limited to a lower vertical direction.

Figure 25:
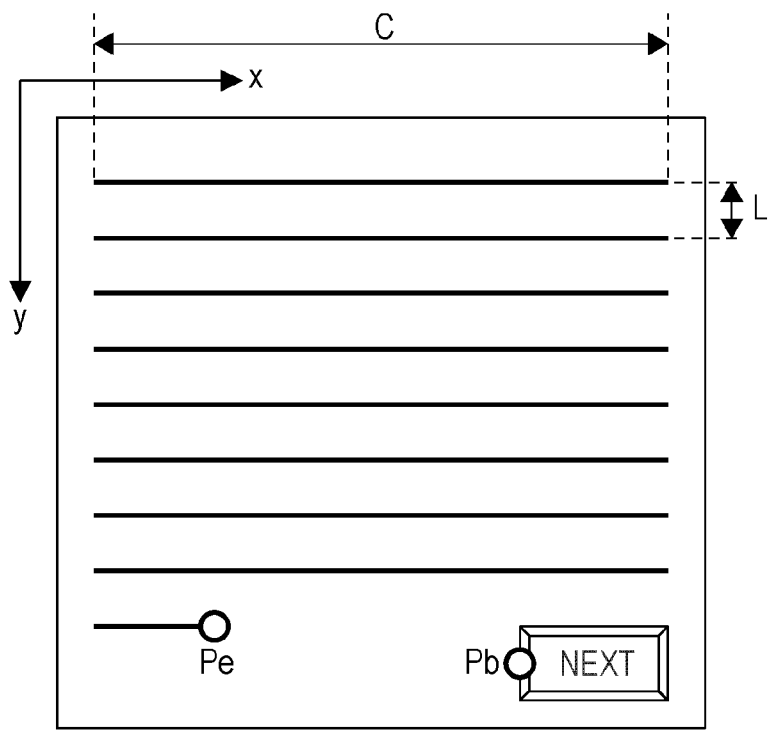
FIG. 25 is a diagram illustrating an example of document data processed in a third embodiment.

As schematically illustrated in FIG. 25, this embodiment discusses an example in which the button is arranged in such a manner that the characteristic gaze movement is caused to occur in the reading direction.

For example, as illustrated in FIG. 25, the line spacing L and the maximum line length C are the same as those in the first embodiment; however, the end position Pe of the last line is not at the right end of the line, but is relatively on the left side. In such a case, it may be difficult in some cases to arrange the button on the further left in terms of the detection of the gaze movement. Therefore, in this embodiment, as illustrated in FIG. 25, the button is arranged one line below the last line, on the right side a certain length from the end of the last line, for example, thereby facilitating the detection of the gaze movement from the end of the last line to the button. Also in this embodiment, it is assumed that the left end of the button is set as the button position Pb.

Figure 26:
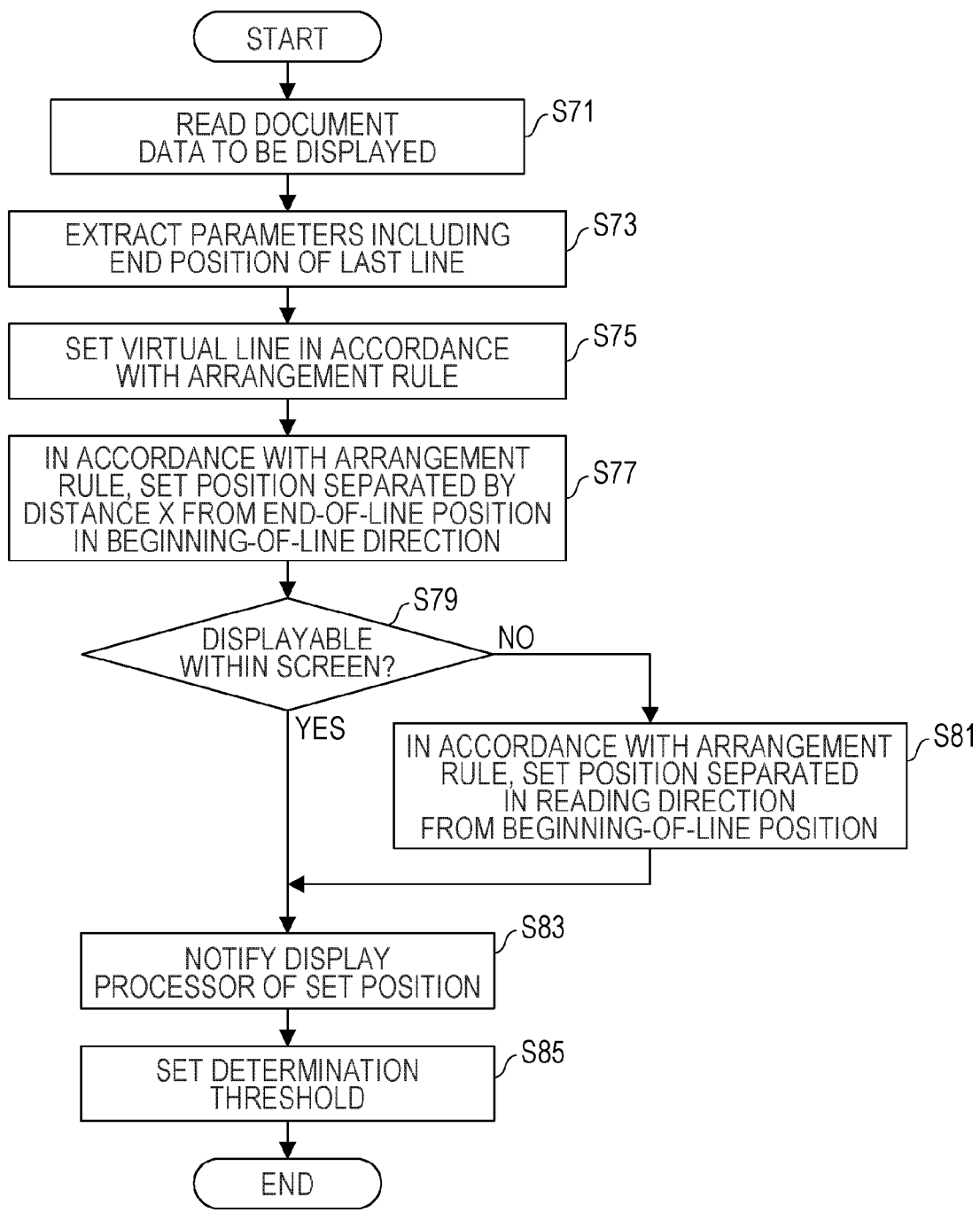
FIG. 26 is a flowchart of a process according to the third embodiment.

For example, in response to an instruction from the input unit 109, the position determining unit 1032 of the document data processor 103 reads document data stored in the first data storage unit 104 (step S71 in FIG. 26). The position determining unit 1032 extracts, from the document data, parameters including the end-of-line position of the last line of text included in the document (step S73).

This embodiment assumes the case in which document data such as that illustrated in FIG. 25 described above is displayed. As in FIG. 5, the document includes only text, which includes nine lines written from left to right (which are simplified using solid lines), and it is assumed that the horizontal direction is represented by an x coordinate, and the vertical direction is represented by a y coordinate. In this embodiment, it is assumed that the end of the ninth line (that is, the end of the text) is not at the right end, but is within an x coordinate value of 0 and C. Note that, for the sake of convenience of illustration, the button "next" is already illustrated. However, at this moment, the position of the button "next" is not established yet. It is assumed that the position of the left end of the button is represented by $Pb=(x_b, y_b)$. Similarly, the line spacing L is also extracted.

The position determining unit 1032 sets a virtual line below the last line in accordance with a button arrangement rule included in setting data stored in the first data storage unit 104, and sets the coordinates of the button on this line (step S75).

For example, if the button arrangement rule is a rule that arranges a button one line below the last line, $y_b=y_e+L$ is set. Note that the rule may be one that arranges a button two lines below the last line. In that case, $y_b=y_e+2L$ is set.

Further, in accordance with the button arrangement rule, the position determining unit 1032 sets the position of the button at a position separated by a distance X from the end-of-line position toward the beginning-of-line position (step S77).

The arrangement rule includes a rule that, for example, as in the first embodiment, how far the button to be arranged is to be separated from the end Pe of the last line in a direction opposite to the text reading direction. In this embodiment, it is assumed that a distance that is in the x-axis direction and that is fifty percent of the line length C, that is, a distance $d_x=0.5C$, is specified. Note that fifty percent is only one example, and, as in the first embodiment, there may be cases in which $X=d_x$, $X=d_x+e$, or $X=d_x+2e$.

Once the distance X is determined as above, the x coordinate value of the button is calculated by $x_b=x_e-X$.

Thereafter, the position determining unit 1032 determines whether the set position is a position displayable within the display screen of the display unit 102 (step S79). For example, when the origin of the coordinates of the display range is (0, 0), if the x coordinate value or the y coordinate value becomes a negative value, it is determined that the position is out of the display range. In this process flow so far, the x coordinate value may become a negative value.

If the set position is a displayable position, the process proceeds to step S83. In contrast, if the set position is not a displayable position, the position determining unit 1032 sets a position separated in the reading direction from the beginning position of the last line in accordance with the button arrangement rule (step S81).

In this embodiment, as schematically illustrated in FIG. 25, the button is arranged at a position separated by a certain distance Y in the reading direction. For example, on the basis of the setting $d_x=0.5C$, an x coordinate value $x_b=x_e+Y=x_e+0.5C$ may be adopted.

Further, a modification that is inversion of the direction in the first embodiment is also possible. That is, a gaze detection error is taken into consideration, and a modification such as $Y=0.5C+e$ or $Y=0.5C+2e$ is possible.

In addition, 0.5C is only one example, and another value may be adopted. Note that the value is set such that the right end of the button does not exceed the display range.

Note that the y-coordinate value may be set in accordance with step S75, or another value may be set as the y-coordinate value.

Thereafter, the position determining unit 1032 notifies the display processor 1031 of the set position data (step S83). Since a process performed by the display processor 1031 is the same as or similar to that in the first embodiment, a description thereof is omitted.

Further, the position determining unit 1032 calculates a determination threshold M4th for determining whether the last line has been read, and outputs the determination threshold M4th to the area setting unit 107 (step S85).

Also in this embodiment, in the case where the positions set in step S75 and S77 are adopted, a process that is the same as or similar to that in the first embodiment is performed.

In addition, in the case where the position set in step S81 is used, for example, the determination threshold M4th is the same as horizontal inversion of the example described in the first embodiment. For example, the determination threshold M4th may be set as Y−2e, or, the length v of a range that is readable at one time is taken into consideration, and the determination threshold M4th may be set as Y−2e−2v.

Note that, since the movement direction is different, data of the movement direction (+x-axis direction in this case) is also added to the determination threshold M4th, and the data is output to the area setting unit 107.

Therefore, in step S37 in the process flow illustrated in FIG. 18, the determination unit 106 determines whether the movement distance in a certain direction, that is, the same direction as the reading direction, is greater than or equal to the determination threshold M4th for the last line.

By executing the above-described process, the button position is changed in accordance with the end position of the last line to a position at which whether the text has been read to the last line is determinable, and it becomes possible to arrange the button at that position. Further, it also becomes possible to calculate the determination threshold for the last line, which is used in the above-described process of determining whether text has been read.

Fourth Embodiment

In the first to third embodiments, a process assuming a document of one page has been described. In the case of presenting a document of a plurality of pages, if the button position is different on the pages, a user who is a reader may become puzzled.

For example, as illustrated in FIG. 27, regarding a first document illustrated on the left, the end position of the last line reaches the right end; however, regarding a second document illustrated on the right, the end position of the last line is not at the right end, but is toward the left end. When these documents are individually processed, in the above-described embodiments, the button is arranged at the left end in the first document, and the button is arranged on the lower side or the right side in the second document.

Therefore, in this embodiment, by performing a process described using FIGS. 28 to 32, while the button is arranged at the same position on a plurality of pages as much as possible, it becomes possible to determine whether the text has been read to the last line in accordance with the gaze movement to this button.

Figure 28:
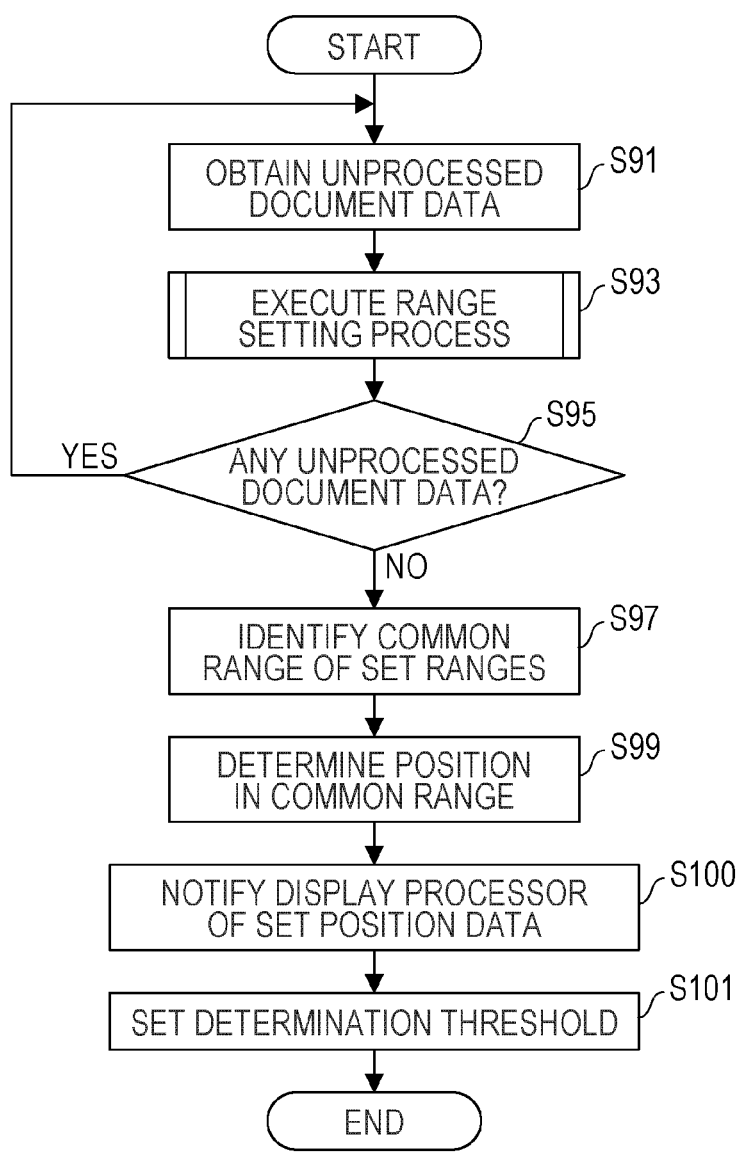
FIG. 28 is a flowchart of a process according to the fourth embodiment.
Figure 29:
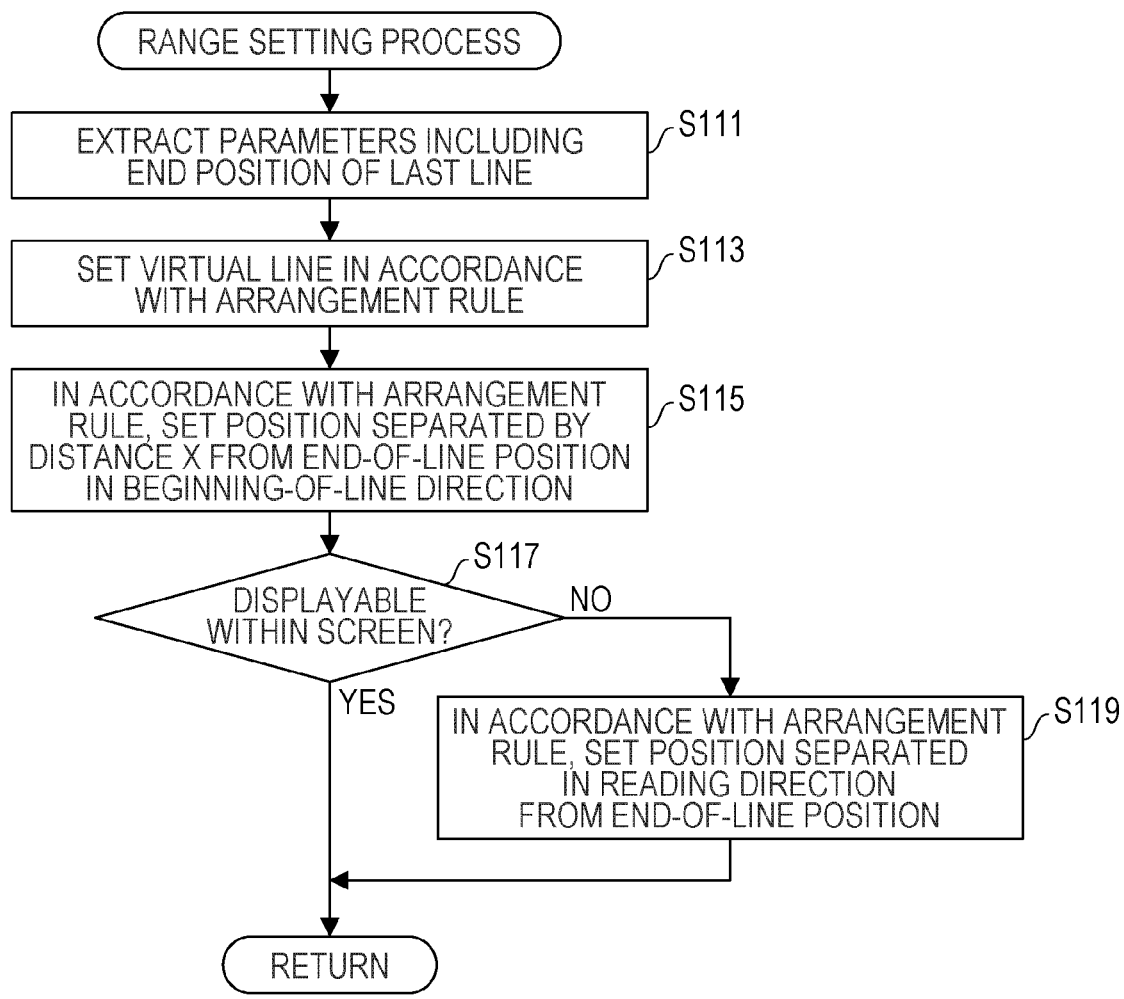
FIG. 29 is a flowchart of a range setting process.

First, the position determining unit 1032 reads unprocessed document data from the first data storage unit 104 (step S91 in FIG. 28). The position determining unit 1032 executes a range setting process on the read document data (step S93). The range setting process will be described using FIG. 29.

First, the position determining unit 1032 extracts, from the document data, parameters including the end position of the last line of text included in the document (step S111). This step is the same as step S3 in the first embodiment. Note that the position of the left end of the button is represented by Pbi=($x_{bi}$, $y_{bi}$), and i represents a page number or a document number.

In this step, the end-of-line position of the last line Pei=($x_{ei}$, $y_{ei}$) is extracted, and the line spacing L is extracted.

The position determining unit 1032 sets a virtual line below the last line in accordance with a button arrangement rule included in setting data stored in the first data storage unit 104, and sets the coordinates of the button on this line (step S113).

For example, if the button arrangement rule is a rule that arranges a button one line below the last line, $y_b=y_e+L$ is set.

Note that the rule may be one that arranges a button two lines below the last line. In that case, $y_b=y_e+2L$ is set.

Further, in accordance with the button arrangement rule, the position determining unit 1032 sets a range that is separated by a distance X from the end-of-line position toward the beginning-of-line position as a button arrangement range (step S115).

For example, X=0.3C is set, and the button arrangement range is set as $x_{bi} \le y_{ei}-0.3C$. Note that X=0.3C is only one example, and another value may be adopted. Also in this case, a gaze detection error may be taken into consideration.

Thereafter, the position determining unit 1032 determines whether the set arrangement range is a range that is displayable within the display screen of the display unit 102 (step S117). For example, when the origin of the coordinates of the display range is (0, 0), if the x coordinate value or the y coordinate value becomes a negative value, it is determined that the set arrangement range is not displayable within the display range. In this process flow so far, the maximum value of the x coordinate value may become a negative value. In this case, it is determined that the set arrangement range is not displayable.

If the set range is a displayable range, the process returns to the calling process. In contrast, if the set range is not within a displayable range, the document data processor 103 sets a position separated in the reading direction from the end position of the last line in accordance with the button arrangement rule (step S119). The process returns to the calling process.

For example, a range that is separated by a certain distance in the reading direction, such as $x_{bi} \ge y_{ei}+0.3C$, is set. Note that 0.3C is only one example, and another value may be adopted. Also in this case, a gaze detection error may be taken into consideration.

Note that, although the above-described example discusses an example in which no range is set in the y-axis direction, a range may also be set in the y-axis direction.

Figure 30:
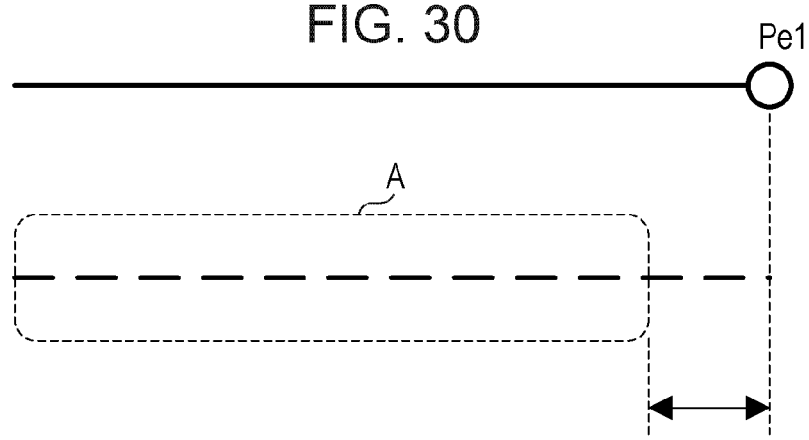
FIG. 30 is a diagram illustrating an example of a display range set for a first document.
Figure 31:
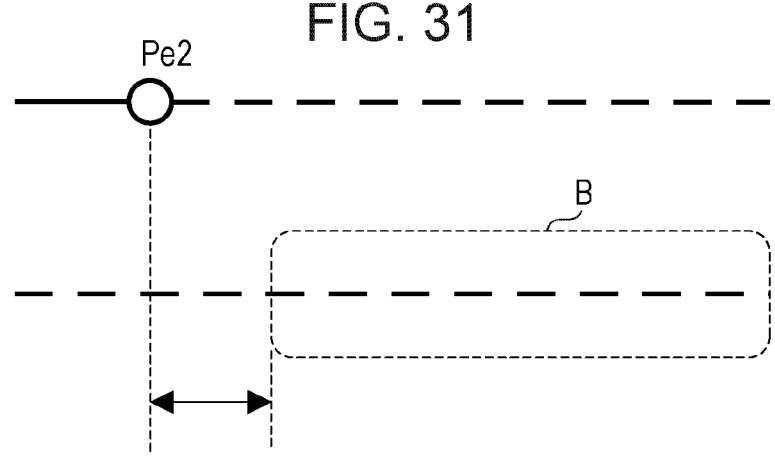
FIG. 31 is a diagram illustrating an example of a display range set for a second document.

For example, regarding the first document illustrated in FIG. 27, since the range set in step S115 is displayable, for example, a range A like that illustrated in FIG. 30 is set. The range A is set on the left side, one line below the last line. In contrast, regarding the second document illustrated in FIG. 27, because the range set in step S115 is not displayable, for example, a range B like that illustrated in FIG. 31 is set. The range B is set on the right side, one line below the last line.

The description now returns to the process illustrated in FIG. 28. The position determining unit 1032 determines whether there is unprocessed document data (step S95). If there is unprocessed document data, the process returns to step S91. In contrast, if there is no unprocessed document data, the position determining unit 1032 identifies a common range of the set ranges (step S97)

Figure 32:
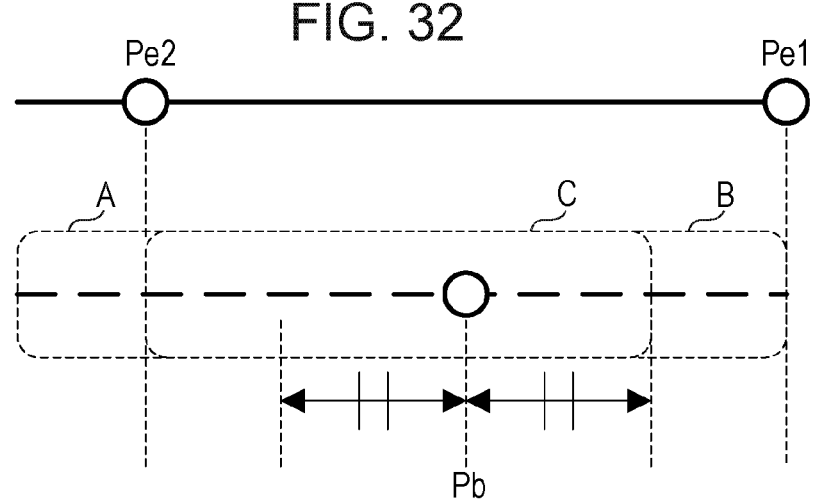
FIG. 32 is a diagram for describing a common display range.

When the examples illustrated in FIG. 30 and FIG. 31 are placed one over the other, the result is like that illustrated in FIG. 32. In the example illustrated in FIG. 32, a common range C of the range A and the range B is identified. The common range C is represented as $x_{e2}+0.3C \le x_b \le x_{e1}-0.3C$.

Note that, in this step, the common range C is undetectable in some cases. In these cases, the button position is determined for each of the documents.

The position determining unit 1032 determines the button position in the common range C (step S99). For example, the intermediate position is adopted. In the case illustrated in FIG. 32, $(x_{e1}+x_{e2})/2$ is obtained as the intermediate position. In the case of two pages, the intermediate position may simply be the midpoint between the end-of-line positions. However, in the case of three or more pages, the intermediate position is not simply obtained. For example, the barycenter of the common range may be used.

Thereafter, the position determining unit 1032 notifies the display processor 1031 of the set position data (step S100). Since a process performed by the display processor 1031 is the same as or similar to that in the first embodiment, a description thereof is omitted.

Further, the position determining unit 1032 calculates a determination threshold for determining whether the last line of each document has been read, and outputs the determination threshold to the area setting unit 107 (step S101).

Once the button position is determined, as has been described in the first embodiment, the difference between the x-coordinate value of the end position of the last line and the x-coordinate value of the button position may simply be set as the determination threshold; a gaze detection error may be taken into consideration; or a length corresponding to a range that is readable at one time may be taken into consideration.

By executing the above-described process, it is possible to have the common button position even when there are differences in the end position of the last line of text included in a plurality of documents, thereby enabling the reader to continue reading without being puzzled.

Although the embodiments have been described as above, the embodiments are not limited to the above-described examples. For example, the above-described functional block configuration of the information processing apparatus is only one example and may not match a program module configuration in some cases.

Further, regarding the process flows, the order of the steps may be changed or a plurality of steps may be executed in parallel as long as the processing result remains unchanged.

In addition, although the above-described examples discuss the case in which one button is arranged, a plurality of buttons may be arranged. In this case, if the position of a button closest to the end position of the last line is determined by the above-described process, and then the other button(s) is/are arranged at farther positions near this button, the same determination threshold is usable in the process of determining whether text has been read.

In addition, in the case where the displayed content changes in response to a screen enlargement/reduction instruction, it is preferable that the button be arranged again.

Further, the relationship between the end position of the last line and the button position may be accumulated, and, if the same end position of the last line is detected later, the already-calculated button position may be read and used.

Further, the timing and duration of allowing the button to be pressed (validating a function assigned to the button) may be modified in various ways. For example, the button may be allowed to be pressed at timing at which lines other than the last line are completely read, or the button may be allowed to be pressed at timing at which it is confirmed that text has been completely read to the last line. Further, the button may be allowed to be pressed only for a certain duration from when it is confirmed that text has been completely read to the last line. Alternatively, the button may be allowed to be pressed only during a period of time in which the user is determined to be looking at the button.

Further, it is possible to make various settings for the arrangement rule. For example, it is possible to make the settings using a vector, or a function may be prepared.

Further, an embodiment combining the second and third embodiments is possible. For example, the button arrangement position may be switched among being arranged in a direction opposite to the reading direction, arranged in the reading direction, and arranged in a lower vertical direction in accordance with the end position of the last line. In addition, these arrangement positions may be prioritized in advance, and, if one of the arrangement positions is not included in the displayable range, the button may be arranged at the next one of the arrangement positions in the priority order.

Further, although the examples in which one text is arranged on one page have been discussed above, the embodiments are also applicable to cases in which a plurality of texts are arranged, and a button is arranged for each of the texts.

Further, although the examples in which no content other than text is included have been discussed above, images and other types of content may be arranged in some cases. And, the same applies to the content, in the determination of whether the content has been finished reading. In such cases, after the button position may be tentatively determined, it may be determined whether the button does not overlap other content, and then the button position may be finally determined. If the button position overlaps other content, another candidate position is determined, and it is determined whether this candidate position does not overlap other content.

Further, since a cursor is moved in order to click the button, the button position may be determined by taking into consideration the cursor position. When the user holds a tablet terminal in one hand, a position that the user is able to easily operate, which is assumed in accordance with the use environment, such as a touch position assumed in accordance with a range where a finger of the hand of the user which is holding the tablet terminal is reachable, may be adopted in some cases. For example, when the user is holding a tablet terminal in the right hand, if the button is arranged in the lower right rather than the lower left, it is considered that the button is more easily operated with the right hand.

Figure 33:
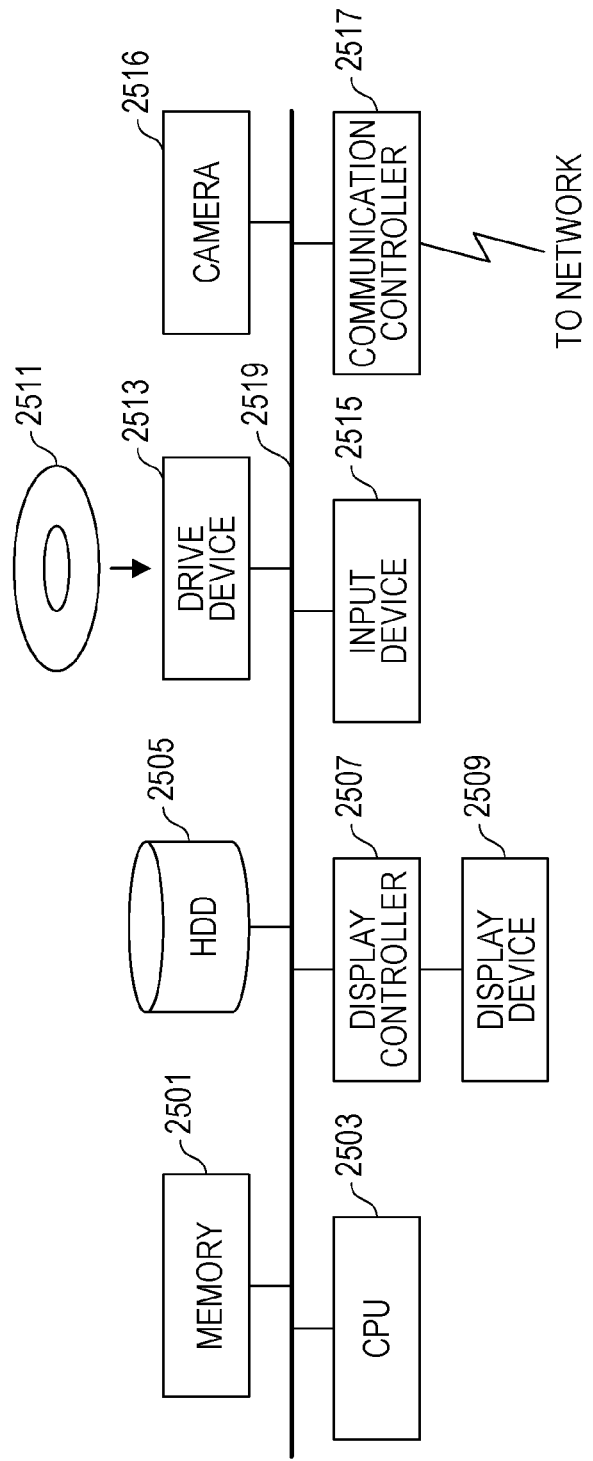
FIG. 33 is a functional block diagram of a computer.

Note that the above-described information processing apparatus 100 is a computer apparatus. As illustrated in FIG. 33, a memory 2501, a central processing unit (CPU) 2503, a hard disk drive (HDD) 2505, a display controller 2507 connected to a display device 2509, a drive device 2513 for a removable disk 2511, an input device 2515, a communication controller 2517 for connecting to a network, and a camera 2516 for capturing an image of a user in order to detect the user's gaze are connected by a bus 2519. An operating system (OS) and an application program for performing processes in the embodiments are stored in the HDD 2505, and, when the CPU 2503 executes the application program, the program is read from the HDD 2505 to the memory 2501. In accordance with the details of processing of the application program, the CPU 2503 controls the display controller 2507, the communication controller 2517, and the drive device 2513 to perform certain operations. In addition, although data being processed is mainly stored in the memory 2501, the data may be stored in the HDD 2505. In the embodiments, an application program for performing processes described in the embodiments is stored in the computer-readable removable disk 2511 and distributed, and installed from the drive device 2513 to the HDD 2505. In some cases, the application program may be installed in the HDD 2505 via a network, such as the Internet, and the communication controller 2517. Such a computer apparatus realizes various functions such as those described above by organic cooperation between hardware such as the above-described CPU 2503 and memory 2501 and a program such as the above-described application program.

The above-described embodiments are summarized as below.

An information processing method according to the embodiments includes: (A) identifying an end position of a last line of a plurality of lines included in text subjected to determination of whether the text has been read, by detecting movement corresponding to a newline at a gaze position on a display screen; (B) determining a display position at which movement of the gaze position that is greater than or equal to a given distance from the identified end position of the last line is detected; and (C) displaying a button for entering that the text has been read, at the determined display position on the display screen.

In some cases, it is difficult to reliably determine whether the last line has been read by simply checking the text for movement corresponding to a newline at the gaze position. Therefore, by arranging the button as described above, it becomes possible to confirm that the text has been read to the last line. Note that the button is one type of display object serving as a goal, and a display object other than the button may be used.

In some cases, the above-described display position is a position at which movement of the gaze position that is greater than or equal to a given distance in a direction opposite to a direction in which the text is read is detected. This is highly compatible with a process of detecting movement of the gaze position corresponding to a newline.

In addition, there are some cases in which the above-described display position is a position at which movement of the gaze position that is greater than or equal to a given distance in a vertical direction with respect to a direction in which the text is read is detected. By detecting a characteristic gaze movement, it is possible to confirm in a stable manner the fact that the last line has been read.

Further, the above-described display position may be a position at which movement of the gaze position that is greater than or equal to a given distance in a direction identical to a direction in which the text is read is detected. By detecting a characteristic gaze movement, it is possible to confirm in a stable manner the fact that the last line has been read.

Further, the above-described information processing method may calculate a movement distance threshold for the last line, which is used in determination of whether the text has been read, based on the given distance. Accordingly, it is possible to appropriately determine whether the last line has been read. Note that, in addition to the threshold, data of the direction of movement may also be included.

Further, the above-described determining method may include a process including (b1) identifying an end position of a last line of each of a plurality of texts; (b2) for each of the plurality of texts, calculating a display position range in which movement of the gaze position that is greater than or equal to a given distance from the identified end position of the last line is detected; and (b3) determining a display position of the button in a range in which the display position ranges calculated for the plurality of texts overlap. For example, by having a common button position for text displayed over a plurality of pages, the reader is able to move his/her gaze to the button in a stable manner, thereby facilitating the detection of the gaze movement.

In addition, there are some cases in which the above-described movement distance threshold is obtained by correcting the above-described given distance in accordance with a gaze detection error, a gaze detection error and a length corresponding to a range that is readable at one time, or a gaze detection error, a length corresponding to a range that is readable at one time, and a button length. In some cases, the threshold is determined by taking into consideration various conditions.

Further, the above-described determination process may determine the display position based on a distance obtained by correcting the given distance in accordance with a detection error of the gaze position. Accordingly, the button may be separated from the end position of the last line by an appropriate length.

Note that a program for causing a computer to execute a process such as that described above may be generated. The program is stored in a computer-readable storage medium such as a flexible disk, an optical disc such as a compact-disc read-only memory (CD-ROM), a magneto-optical disc, a semiconductor memory (such as a ROM), or a hard disk, or a storage device. Note that data being processed is temporarily stored in a storage device such as a random-access memory (RAM).

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiments of the present invention have been described in detail, it should be understood that the various changes, substitutions, and alterations could be made hereto without departing from the spirit and scope of the invention.

What is claimed is:

1. An information processing apparatus, comprising:
a memory, and
a processor coupled to the memory and configured to:
obtain data of a number of lines in an object for reading displayed on a display screen,
determine, based on movement of a gaze position of a user, whether a line break has occurred by comparing the movement of the gaze position to a first movement threshold,
determine whether a number of line breaks that have occurred is greater than or equal to a threshold number of line breaks, the threshold number of line breaks being the obtained number of lines,
when the number of line breaks is greater than or equal to the threshold number of line breaks, determine that a last line among the number of lines has been reached,
identify an end position of the last line,
determine a display position of a display component to be gazed by the user after the object has been finished reading, the display position being at a predetermined distance from the end position of the last line,
display the display component at the display position on the display screen,
set a second movement threshold based on an error regarding a gaze detection, the second movement threshold being used for determining whether the user gazes the display component and being shorter than the predetermined distance,
acquire a first gaze position and a second gaze position of the user by the gaze detection,
determine whether a distance from the first gaze position to the second gaze position is equal to or larger than the second movement threshold, and
determine that the display component is gazed by the user when the distance from the first gaze position to the second gaze position is equal to or larger than the second movement threshold.

2. The information processing apparatus according to claim 1,
wherein the display position is greater than or equal to the predetermined distance from the end position of the last line in a direction opposite to a direction in which the object is read.

3. The information processing apparatus according to claim 1,
wherein the display position is greater than or equal to the predetermined distance from the end position of the last line in a vertical direction with respect to a direction in which the object is read.

4. The information processing apparatus according to claim 1,
wherein the display position is greater than or equal to the predetermined distance in a direction identical to a direction in which the text is read.

5. The information processing apparatus according to claim 1,
wherein the processor is configured to identify each end position of each last line of each of a plurality of objects for reading displayed on the display screen,
wherein the processor is configured to calculate, for each of the plurality of objects, each of a plurality of ranges based on each end position and the predetermined distance, and
wherein the processor is configured to determine the display position based on an overlapped range with respect to the ranges.

6. The information processing apparatus according to claim 1,
wherein the second movement threshold is set based on at least one of a length corresponding to a range that is readable at one time, and a size of the display object.

7. The information processing apparatus according to claim 1,
wherein the processor is configured to determine the display position based on a distance obtained by correcting the predetermined distance in accordance with the error.

8. The information processing apparatus according to claim 1,
wherein the processor is configured to perform a determination of whether the distance from the first gaze position to the second gaze position is equal or larger than the second movement threshold, based on detecting movement indicating a newline.

9. The information processing apparatus according to claim 1,
wherein the object for reading includes text of a line configuration having the plurality of lines.

10. The information processing apparatus according to claim 1,
wherein the display component is to be operated by the user after the object has been finished reading.

11. The information processing apparatus according to claim 1,
wherein the display component includes a button for entering that the object has been finished reading.

12. The information processing apparatus according to claim 1, wherein the display component is a button and the button is only made clickable by the user when it is determined that the distance from the first gaze position to the second gaze position is equal to or larger than the second movement threshold.

13. The information processing apparatus according to claim 1, wherein the first movement threshold is different from the second movement threshold.

14. An information processing method, comprising:
obtaining data of a number of lines in an object for reading displayed on a display screen;
determining, based on movement of a gaze position of a user, whether a line break has occurred by comparing the movement of the gaze position to a first movement threshold;
determining whether a number of line breaks that have occurred is greater than or equal to a threshold number of line breaks, the threshold number of line breaks being the obtained number of lines;
when the number of line breaks is greater than or equal to the threshold number of line breaks, determining that a last line among the number of lines has been reached;
identifying an end position of the last line;
determining, by a processor, a display position of a display component to be gazed by the user after the object has been finished reading, the display position being at a predetermined distance from the end position of the last line;
displaying the display component at the display position on the display screen;
setting a second movement threshold based on an error regarding a gaze detection, the second movement threshold being used for determining whether the user gazes the display component and being shorter than the predetermined distance;
acquiring a first gaze position and a second gaze position of the user by the gaze detection;
determining whether a distance from the first gaze position to the second gaze position is equal to or larger than the second movement threshold; and
determining that the display component is gazed by the user when the distance from the first gaze position to the second gaze position is equal to or larger than the second movement threshold.

15. A non-transitory computer-readable recording medium storing a program that causes a computer to execute a procedure, the procedure comprising:
obtaining data of a number of lines in an object for reading displayed on a display screen;
determining, based on movement of a gaze position of a user, whether a line break has occurred by comparing the movement of the gaze position to a first movement threshold;
determining whether a number of line breaks that have occurred is greater than or equal to a threshold number of line breaks, the threshold number of line breaks being the obtained number of lines;
when the number of line breaks is greater than or equal to the threshold number of line breaks, determining that a last line among the number of lines has been reached;
identifying an end position of the last line;
determining a display position of a display component to be gazed by the user after the object has been finished reading, the display position being at a predetermined distance from the end position of the last line;
displaying the display component at the display position on the display screen;
setting a second movement threshold based on an error regarding a gaze detection, the second movement threshold being used for determining whether the user gazes the display component and being shorter than the predetermined distance;
acquiring a first gaze position and a second gaze position of the user by the gaze detection;

determining whether a distance from the first gaze position to the second gaze position is equal to or larger than the second movement threshold; and determining that the display component is gazed by the user when the distance from the first gaze position to the second gaze position is equal to or larger than the second movement threshold.

\* \* \* \* \*